US009833229B2

(12) United States Patent
Hernandez et al.

(10) Patent No.: US 9,833,229 B2
(45) Date of Patent: Dec. 5, 2017

(54) ADJUSTABLE ANCHOR SYSTEMS AND METHODS

(71) Applicant: Medos International Sàrl, Le Locle (CH)

(72) Inventors: Joseph Hernandez, Sandwich, MA (US); Mehmet Ziya Sengun, Canton, MA (US); Gerome Miller, Randolph, MA (US); Gregory R. Whittaker, Stoneham, MA (US); Gary B. McAlister, Franklin, MA (US)

(73) Assignee: MEDOS INTERNATIONAL SÀRL, Le Locle (CH)

( * ) Notice: Subject to any disclaimer, the term of this patent is extended or adjusted under 35 U.S.C. 154(b) by 0 days.

(21) Appl. No.: 14/754,773

(22) Filed: Jun. 30, 2015

(65) Prior Publication Data

US 2015/0297214 A1 Oct. 22, 2015

Related U.S. Application Data

(60) Division of application No. 13/336,151, filed on Dec. 23, 2011, now Pat. No. 9,095,331, which is a
(Continued)

(51) Int. Cl.
*A61B 17/04* (2006.01)
*A61B 17/06* (2006.01)

(52) U.S. Cl.
CPC ...... *A61B 17/0401* (2013.01); *A61B 17/0485* (2013.01); *A61B 17/06114* (2013.01); *A61B 2017/0403* (2013.01); *A61B 2017/044* (2013.01); *A61B 2017/0412* (2013.01); *A61B 2017/0414* (2013.01); *A61B 2017/0445* (2013.01); *A61B 2017/0456* (2013.01); *A61B 2017/0458* (2013.01); *A61B 2017/0464* (2013.01); *A61B 2017/0475* (2013.01);
(Continued)

(58) Field of Classification Search
CPC . A61B 17/04; A61B 17/0401; A61B 17/0485; A61B 2017/0464; A61B 2017/0414; A61B 2017/0445; A61B 2017/044
USPC ........ 606/139, 144, 145, 148, 228, 230, 232
See application file for complete search history.

(56) References Cited

U.S. PATENT DOCUMENTS

| 2,566,625 | A | 9/1951 | Nagelmann |
| 2,600,395 | A | 6/1952 | Domoj et al. |

(Continued)

FOREIGN PATENT DOCUMENTS

| AU | 2008229746 A1 | 10/2008 |
| CA | 2772500 A1 | 9/2013 |

(Continued)

OTHER PUBLICATIONS

[No Author Listed] Arthroscopic Knot Tying Manual 2005. DePuy Mitek. 27 pages.
(Continued)

*Primary Examiner* — Vy Bui

(57) ABSTRACT

An adjustable anchor system provides for securing tissue to bone and includes an anchor with a collapsible suture loop affixed thereto and a tissue suture connected to the collapsible suture loop. After the tissue suture is loaded into the tissue and the anchor implanted into the bone the collapsible loop is collapsed to tension the tissue suture.

22 Claims, 26 Drawing Sheets

Related U.S. Application Data continuation-in-part of application No. 12/977,146, filed on Dec. 23, 2010, now Pat. No. 8,821,543.

(52) U.S. Cl.
CPC .............. *A61B 2017/06028* (2013.01); *A61B 2017/06042* (2013.01)

(56) References Cited

U.S. PATENT DOCUMENTS

| | | |
|---|---|---|
| 2,697,624 A | 12/1954 | Thomas et al. |
| 2,758,858 A | 8/1956 | Smith |
| 2,992,029 A | 7/1961 | Russell |
| 3,106,417 A | 10/1963 | Clow |
| 3,131,957 A | 5/1964 | Musto |
| 3,177,021 A | 4/1965 | Benham |
| 3,402,957 A | 9/1968 | Peterson |
| 3,521,918 A | 7/1970 | Hammond |
| 3,565,077 A | 2/1971 | Glick |
| 3,580,256 A | 5/1971 | Wilkinson et al. |
| 3,712,651 A | 1/1973 | Shockley |
| 3,752,516 A | 8/1973 | Mumma |
| 3,873,140 A | 3/1975 | Bloch |
| 4,029,346 A | 6/1977 | Browning |
| 4,036,101 A | 7/1977 | Burnett |
| 4,038,988 A | 8/1977 | Perisse |
| 4,105,034 A | 8/1978 | Shalaby et al. |
| 4,130,639 A | 12/1978 | Shalaby et al. |
| 4,140,678 A | 2/1979 | Shalaby et al. |
| 4,141,087 A | 2/1979 | Shalaby et al. |
| 4,186,921 A | 2/1980 | Fox |
| 4,205,399 A | 6/1980 | Shalaby et al. |
| 4,208,511 A | 6/1980 | Shalaby et al. |
| 4,319,428 A | 3/1982 | Fox |
| 4,403,797 A | 9/1983 | Ragland, Jr. |
| 4,510,934 A | 4/1985 | Batra |
| 4,572,554 A | 2/1986 | Janssen et al. |
| 4,792,336 A | 12/1988 | Hlavacek et al. |
| 4,870,957 A | 10/1989 | Goble et al. |
| 4,946,377 A | 8/1990 | Kovach |
| 4,962,929 A | 10/1990 | Melton, Jr. |
| 4,987,665 A | 1/1991 | Dumican et al. |
| 5,062,344 A | 11/1991 | Gerker |
| 5,098,137 A | 3/1992 | Wardall |
| 5,144,961 A | 9/1992 | Chen et al. |
| 5,156,616 A | 10/1992 | Meadows et al. |
| 5,178,629 A | 1/1993 | Kammerer |
| 5,217,495 A | 6/1993 | Kaplan et al. |
| 5,250,053 A | 10/1993 | Snyder |
| 5,250,054 A | 10/1993 | Li |
| 5,259,846 A | 11/1993 | Granger et al. |
| 5,263,984 A | 11/1993 | Li et al. |
| 5,279,311 A | 1/1994 | Snyder |
| 5,282,809 A | 2/1994 | Kammerer et al. |
| 5,284,485 A | 2/1994 | Kammerer et al. |
| 5,312,423 A | 5/1994 | Rosenbluth et al. |
| 5,318,575 A | 6/1994 | Chesterfield et al. |
| 5,320,629 A | 6/1994 | Noda et al. |
| 5,376,118 A | 12/1994 | Kaplan et al. |
| 5,391,176 A | 2/1995 | de la Torre |
| 5,395,382 A | 3/1995 | DiGiovanni et al. |
| 5,405,352 A | 4/1995 | Weston |
| 5,450,860 A | 9/1995 | O'Connor |
| 5,454,820 A | 10/1995 | Kammerer et al. |
| 5,456,722 A | 10/1995 | McLeod et al. |
| 5,464,427 A | 11/1995 | Curtis et al. |
| 5,464,929 A | 11/1995 | Bezwada et al. |
| 5,472,446 A | 12/1995 | de la Torre |
| 5,527,323 A | 6/1996 | Jervis et al. |
| 5,534,011 A | 7/1996 | Greene, Jr. et al. |
| 5,540,703 A | 7/1996 | Barker, Jr. et al. |
| 5,549,618 A | 8/1996 | Fleenor et al. |
| 5,562,684 A | 10/1996 | Kammerer |
| 5,569,306 A | 10/1996 | Thal |
| 5,571,139 A | 11/1996 | Jenkins, Jr. |
| 5,573,286 A | 11/1996 | Rogozinski |
| 5,591,207 A | 1/1997 | Coleman |
| 5,593,189 A | 1/1997 | Little |
| 5,595,751 A | 1/1997 | Bezwada et al. |
| 5,597,579 A | 1/1997 | Bezwada et al. |
| 5,607,687 A | 3/1997 | Bezwada et al. |
| 5,618,552 A | 4/1997 | Bezwada et al. |
| 5,620,698 A | 4/1997 | Bezwada et al. |
| 5,628,756 A | 5/1997 | Barker |
| 5,645,850 A | 7/1997 | Bezwada et al. |
| 5,647,616 A | 7/1997 | Hamilton |
| 5,647,874 A | 7/1997 | Hayhurst |
| 5,648,088 A | 7/1997 | Bezwada et al. |
| 5,667,528 A | 9/1997 | Colligan |
| 5,683,417 A | 11/1997 | Cooper |
| 5,683,419 A | 11/1997 | Thal |
| 5,685,037 A | 11/1997 | Fitzner et al. |
| 5,698,213 A | 12/1997 | Jamiolkowski et al. |
| 5,700,583 A | 12/1997 | Jamiolkowski et al. |
| 5,702,397 A | 12/1997 | Goble et al. |
| 5,709,708 A | 1/1998 | Thal |
| 5,716,368 A | 2/1998 | de la Torre et al. |
| 5,725,556 A | 3/1998 | Moser et al. |
| 5,728,109 A | 3/1998 | Schulze et al. |
| 5,741,332 A | 4/1998 | Schmitt |
| 5,749,898 A | 5/1998 | Schulze et al. |
| 5,782,864 A | 7/1998 | Lizardi |
| 5,814,069 A | 9/1998 | Schulze et al. |
| 5,859,150 A | 1/1999 | Jamiolkowski et al. |
| 5,899,920 A | 5/1999 | DeSatnick et al. |
| 5,941,900 A | 8/1999 | Bonutti |
| 5,964,783 A | 10/1999 | Grafton et al. |
| 5,971,447 A | 10/1999 | Steck, III |
| 5,989,252 A | 11/1999 | Fumex |
| 6,024,758 A | 2/2000 | Thal |
| 6,045,574 A | 4/2000 | Thal |
| 6,143,017 A | 11/2000 | Thal |
| 6,221,084 B1 | 4/2001 | Fleenor |
| 6,267,766 B1 | 7/2001 | Burkhart |
| 6,296,659 B1 | 10/2001 | Foerster |
| 6,319,271 B1 | 11/2001 | Schwartz |
| 6,322,112 B1 | 11/2001 | Duncan |
| 6,517,578 B2 | 2/2003 | Hein |
| 6,527,794 B1 | 3/2003 | McDevitt et al. |
| 6,527,795 B1 | 3/2003 | Lizardi |
| 6,540,750 B2 | 4/2003 | Burkhart |
| 6,547,807 B2 | 4/2003 | Chan et al. |
| 6,596,015 B1 | 7/2003 | Pitt et al. |
| 6,641,596 B1 | 11/2003 | Lizardi |
| 6,641,597 B2 | 11/2003 | Burkhart et al. |
| 6,652,563 B2 | 11/2003 | Dreyfuss |
| 6,660,023 B2 | 12/2003 | McDevitt et al. |
| 6,689,154 B2 | 2/2004 | Bartlett |
| 6,716,234 B2 | 4/2004 | Grafton et al. |
| 6,767,037 B2 | 7/2004 | Wenstrom, Jr. |
| 6,818,010 B2 | 11/2004 | Eichhorn et al. |
| 6,887,259 B2 | 5/2005 | Lizardi |
| 6,923,824 B2 | 8/2005 | Morgan et al. |
| 6,994,719 B2 | 2/2006 | Grafton |
| 7,029,490 B2 | 4/2006 | Grafton et al. |
| 7,048,754 B2 | 5/2006 | Martin et al. |
| 7,081,126 B2 | 7/2006 | McDevitt et al. |
| 7,217,279 B2 | 5/2007 | Reese |
| 7,226,469 B2 | 6/2007 | Benavitz et al. |
| 7,235,090 B2 | 6/2007 | Buckman et al. |
| 7,285,124 B2 | 10/2007 | Foerster |
| 7,309,337 B2 | 12/2007 | Colleran et al. |
| 7,338,502 B2 | 3/2008 | Rosenblatt |
| 7,381,213 B2 | 6/2008 | Lizardi |
| 7,390,332 B2 | 6/2008 | Selvitelli et al. |
| 7,455,684 B2 | 11/2008 | Gradel et al. |
| 7,582,105 B2 | 9/2009 | Kolster |
| 7,601,165 B2 | 10/2009 | Stone |
| 7,651,509 B2 | 1/2010 | Bojarski et al. |
| 7,654,321 B2 | 2/2010 | Zazovsky et al. |
| 7,658,750 B2 | 2/2010 | Li |
| 7,658,751 B2 | 2/2010 | Stone et al. |
| 7,682,374 B2 | 3/2010 | Foerster et al. |
| 7,695,495 B2 | 4/2010 | Dreyfuss |

(56) References Cited

U.S. PATENT DOCUMENTS

| | | |
|---|---|---|
| 7,703,372 B1 | 4/2010 | Shakespeare |
| 7,803,173 B2 | 9/2010 | Burkhart et al. |
| 7,875,043 B1 | 1/2011 | Ashby et al. |
| 7,883,528 B2 | 2/2011 | Grafton et al. |
| 7,883,529 B2 | 2/2011 | Sinnott et al. |
| 7,905,903 B2 | 3/2011 | Stone et al. |
| 7,905,904 B2 | 3/2011 | Stone et al. |
| 7,959,650 B2 | 6/2011 | Kaiser et al. |
| 7,981,140 B2 | 7/2011 | Burkhart |
| 8,012,171 B2 | 9/2011 | Schmieding |
| 8,088,130 B2 | 1/2012 | Kaiser et al. |
| 8,088,146 B2 | 1/2012 | Wert et al. |
| 8,114,128 B2 | 2/2012 | Cauldwell et al. |
| 8,118,836 B2 | 2/2012 | Denham et al. |
| 8,137,382 B2 | 3/2012 | Denham et al. |
| 8,231,653 B2 | 7/2012 | Dreyfuss |
| 8,231,654 B2 | 7/2012 | Kaiser et al. |
| 8,419,769 B2 | 4/2013 | Thal |
| 8,545,535 B2 * | 10/2013 | Hirotsuka .......... A61B 17/0401 606/232 |
| 8,608,758 B2 * | 12/2013 | Singhatat .......... A61B 17/0469 606/139 |
| 8,790,369 B2 | 7/2014 | Orphanos et al. |
| 8,790,370 B2 | 7/2014 | Spenciner et al. |
| 8,814,905 B2 | 8/2014 | Sengun et al. |
| 8,821,543 B2 | 9/2014 | Hernandez et al. |
| 8,821,544 B2 | 9/2014 | Sengun et al. |
| 8,821,545 B2 | 9/2014 | Sengun |
| 8,894,684 B2 | 11/2014 | Sengun |
| 8,974,495 B2 | 3/2015 | Hernandez et al. |
| 9,017,381 B2 | 4/2015 | Kaiser et al. |
| 9,034,013 B2 | 5/2015 | Sengun |
| 9,060,763 B2 | 6/2015 | Sengun |
| 9,060,764 B2 | 6/2015 | Sengun |
| 9,095,331 B2 | 8/2015 | Hernandez et al. |
| 9,179,908 B2 | 11/2015 | Sengun |
| 9,192,373 B2 | 11/2015 | Sengun |
| 9,198,653 B2 | 12/2015 | Sengun et al. |
| 9,271,716 B2 | 3/2016 | Sengun |
| 9,345,468 B2 | 5/2016 | Sengun et al. |
| 9,345,567 B2 | 5/2016 | Sengun |
| 9,532,778 B2 | 1/2017 | Sengun et al. |
| 2002/0019649 A1 | 2/2002 | Sikora et al. |
| 2002/0029066 A1 | 3/2002 | Foerster |
| 2003/0004545 A1 | 1/2003 | Burkhart et al. |
| 2003/0050667 A1 | 3/2003 | Grafton et al. |
| 2003/0120309 A1 | 6/2003 | Colleran et al. |
| 2003/0130695 A1 | 7/2003 | McDevitt et al. |
| 2003/0229362 A1 | 12/2003 | Chan et al. |
| 2004/0093031 A1 | 5/2004 | Burkhart et al. |
| 2004/0098050 A1 | 5/2004 | Foerster et al. |
| 2004/0153074 A1 | 8/2004 | Bojarski et al. |
| 2004/0172062 A1 | 9/2004 | Burkhart |
| 2004/0236373 A1 | 11/2004 | Anspach |
| 2005/0033363 A1 | 2/2005 | Bojarski et al. |
| 2005/0119696 A1 | 6/2005 | Walters et al. |
| 2005/0137624 A1 | 6/2005 | Fallman |
| 2005/0187577 A1 | 8/2005 | Selvitelli et al. |
| 2005/0251208 A1 | 11/2005 | Elmer et al. |
| 2006/0106423 A1 | 5/2006 | Weisel et al. |
| 2006/0178680 A1 | 8/2006 | Nelson et al. |
| 2006/0178702 A1 | 8/2006 | Pierce et al. |
| 2006/0293710 A1 | 12/2006 | Foerster et al. |
| 2007/0027476 A1 | 2/2007 | Harris et al. |
| 2007/0032792 A1 | 2/2007 | Collin et al. |
| 2007/0060922 A1 | 3/2007 | Dreyfuss |
| 2007/0083236 A1 | 4/2007 | Sikora et al. |
| 2007/0135843 A1 | 6/2007 | Burkhart |
| 2007/0150003 A1 | 6/2007 | Dreyfuss et al. |
| 2007/0156148 A1 | 7/2007 | Fanton et al. |
| 2007/0156149 A1 | 7/2007 | Fanton et al. |
| 2007/0156150 A1 | 7/2007 | Fanton et al. |
| 2007/0156176 A1 | 7/2007 | Fanton et al. |
| 2007/0219557 A1 | 9/2007 | Bourque et al. |
| 2007/0219558 A1 | 9/2007 | Deutsch |
| 2007/0225719 A1 | 9/2007 | Stone et al. |
| 2007/0239209 A1 | 10/2007 | Fallman |
| 2008/0009901 A1 | 1/2008 | Redmond et al. |
| 2008/0009904 A1 | 1/2008 | Bourque et al. |
| 2008/0027446 A1 | 1/2008 | Stone et al. |
| 2008/0065114 A1 | 3/2008 | Stone et al. |
| 2008/0077182 A1 | 3/2008 | Geissler et al. |
| 2008/0091237 A1 | 4/2008 | Schwartz et al. |
| 2008/0103528 A1 | 5/2008 | Zirps et al. |
| 2008/0140092 A1 | 6/2008 | Stone et al. |
| 2008/0147063 A1 | 6/2008 | Cauldwell et al. |
| 2008/0188893 A1 | 8/2008 | Selvitelli et al. |
| 2008/0195205 A1 | 8/2008 | Schwartz |
| 2008/0208265 A1 | 8/2008 | Frazier et al. |
| 2008/0228265 A1 | 9/2008 | Spence et al. |
| 2008/0255613 A1 | 10/2008 | Kaiser et al. |
| 2008/0275469 A1 | 11/2008 | Fanton et al. |
| 2008/0312689 A1 | 12/2008 | Denham et al. |
| 2009/0023984 A1 | 1/2009 | Stokes et al. |
| 2009/0036905 A1 | 2/2009 | Schmieding |
| 2009/0054928 A1 | 2/2009 | Denham et al. |
| 2009/0062850 A1 | 3/2009 | Ken |
| 2009/0062854 A1 | 3/2009 | Kaiser et al. |
| 2009/0082805 A1 | 3/2009 | Kaiser et al. |
| 2009/0082807 A1 | 3/2009 | Miller et al. |
| 2009/0088798 A1 | 4/2009 | Snyder et al. |
| 2009/0099598 A1 | 4/2009 | McDevitt et al. |
| 2009/0138042 A1 | 5/2009 | Thal |
| 2009/0234387 A1 | 9/2009 | Miller et al. |
| 2009/0281568 A1 | 11/2009 | Cendan et al. |
| 2009/0281581 A1 | 11/2009 | Berg |
| 2009/0287246 A1 | 11/2009 | Cauldwell et al. |
| 2009/0306711 A1 | 12/2009 | Stone et al. |
| 2009/0312776 A1 | 12/2009 | Kaiser et al. |
| 2009/0312794 A1 | 12/2009 | Nason et al. |
| 2009/0318958 A1 | 12/2009 | Ochiai |
| 2010/0004683 A1 | 1/2010 | Hoof et al. |
| 2010/0016892 A1 | 1/2010 | Kaiser et al. |
| 2010/0094425 A1 | 4/2010 | Bentley et al. |
| 2010/0162882 A1 | 7/2010 | Shakespeare |
| 2010/0204730 A1 | 8/2010 | Maiorino et al. |
| 2010/0249809 A1 | 9/2010 | Singhatat et al. |
| 2010/0249834 A1 | 9/2010 | Dreyfuss |
| 2010/0256677 A1 | 10/2010 | Albertorio et al. |
| 2010/0292732 A1 | 11/2010 | Hirotsuka et al. |
| 2010/0292792 A1 | 11/2010 | Stone et al. |
| 2011/0022083 A1 | 1/2011 | DiMatteo et al. |
| 2011/0022084 A1 | 1/2011 | Sengun et al. |
| 2011/0077667 A1 | 3/2011 | Singhatat et al. |
| 2011/0098727 A1 | 4/2011 | Kaiser et al. |
| 2011/0152928 A1 | 6/2011 | Colleran et al. |
| 2011/0190815 A1 | 8/2011 | Saliman |
| 2011/0208239 A1 | 8/2011 | Stone et al. |
| 2011/0208240 A1 | 8/2011 | Stone et al. |
| 2011/0213416 A1 | 9/2011 | Kaiser |
| 2011/0238111 A1 | 9/2011 | Frank |
| 2011/0264140 A1 | 10/2011 | Lizardi et al. |
| 2011/0264141 A1 | 10/2011 | Denham et al. |
| 2011/0270278 A1 | 11/2011 | Overes et al. |
| 2012/0046693 A1 | 2/2012 | Denham et al. |
| 2012/0053630 A1 | 3/2012 | Denham et al. |
| 2012/0059417 A1 | 3/2012 | Norton et al. |
| 2012/0101523 A1 | 4/2012 | Wert et al. |
| 2012/0101524 A1 | 4/2012 | Bennett |
| 2012/0130423 A1 | 5/2012 | Sengun et al. |
| 2012/0130424 A1 | 5/2012 | Sengun et al. |
| 2012/0150223 A1 | 6/2012 | Manos et al. |
| 2012/0165864 A1 | 6/2012 | Hernandez et al. |
| 2012/0179199 A1 | 7/2012 | Hernandez et al. |
| 2012/0253389 A1 | 10/2012 | Sengun et al. |
| 2012/0253390 A1 | 10/2012 | Sengun |
| 2012/0296375 A1 | 11/2012 | Thal |
| 2013/0110165 A1 | 5/2013 | Burkhart et al. |
| 2013/0158598 A1 | 6/2013 | Lizardi |
| 2013/0261664 A1 | 10/2013 | Spenciner et al. |
| 2013/0296895 A1 | 11/2013 | Sengun |
| 2013/0296896 A1 | 11/2013 | Sengun |
| 2013/0296931 A1 | 11/2013 | Sengun |
| 2013/0296934 A1 | 11/2013 | Sengun |

(56) References Cited

U.S. PATENT DOCUMENTS

| | | |
|---|---|---|
| 2014/0081324 A1 | 3/2014 | Sengun |
| 2014/0107701 A1 | 4/2014 | Lizardi et al. |
| 2014/0188163 A1 | 7/2014 | Sengun |
| 2014/0188164 A1 | 7/2014 | Sengun |
| 2014/0277132 A1 | 9/2014 | Sengun et al. |
| 2014/0330312 A1 | 11/2014 | Spenciner et al. |
| 2014/0343606 A1 | 11/2014 | Hernandez et al. |
| 2014/0343607 A1 | 11/2014 | Sengun et al. |
| 2015/0012038 A1 | 1/2015 | Sengun et al. |
| 2015/0025572 A1 | 1/2015 | Sengun |
| 2015/0045832 A1 | 2/2015 | Sengun |
| 2015/0238183 A1 | 8/2015 | Sengun |
| 2015/0245832 A1 | 9/2015 | Sengun |
| 2015/0313587 A1 | 11/2015 | Lizardi et al. |
| 2016/0128687 A1 | 5/2016 | Sengun |
| 2016/0278761 A1 | 9/2016 | Sengun et al. |
| 2016/0296222 A1 | 10/2016 | Sengun |
| 2017/0000479 A1 | 1/2017 | Sengun et al. |

FOREIGN PATENT DOCUMENTS

| | | |
|---|---|---|
| CN | 2719234 Y | 8/2005 |
| CN | 101252887 A | 8/2008 |
| CN | 101442944 A | 5/2009 |
| CN | 101961256 A | 2/2011 |
| CN | 102113901 A | 7/2011 |
| EP | 0 870 471 A1 | 10/1998 |
| EP | 1 199 035 A1 | 4/2002 |
| EP | 1 707 127 A1 | 10/2006 |
| EP | 2 277 457 A1 | 1/2011 |
| EP | 2 455 003 A2 | 5/2012 |
| EP | 2 572 650 A1 | 3/2013 |
| JP | 2000-512193 A | 9/2000 |
| WO | 95/19139 A1 | 7/1995 |
| WO | 97/17901 A1 | 5/1997 |
| WO | 98/11825 A1 | 3/1998 |
| WO | 98/42261 A1 | 10/1998 |
| WO | 01/06933 A2 | 2/2001 |
| WO | 03/022161 A1 | 3/2003 |
| WO | 2007/005394 A1 | 1/2007 |
| WO | 2007/078281 A2 | 7/2007 |
| WO | 2007/109769 A1 | 9/2007 |

OTHER PUBLICATIONS

[No Author Listed] Gryphon Brochure. DePuy Mitek. 2 pages (undated).

[No Author Listed] Versalok Anchor. Brochure. DePuy Mitek, a Johnson & Johnson company, 92 pages, 2007.

Allcock, The Encyclopedia of Polymer Science, vol. 13, pp. 31-41, Wiley Intersciences, John Wiley & Sons, 1988.

Cohn et al., Biodegradable PEO/PLA block copolymers. J Biomed Mater Res. Nov. 1988;22(11):993-1009.

Cohn et al., Polym Preprint. 1989:30(1):498.

Dahl et al., Biomechanical characteristics of 9 arthroscopic knots. Arthroscopy. Jun. 2010:26(6):813-8.

EP Search Report for Application No. 11190157.5 issued Feb. 27, 2012. (8 pages).

Extended European Search Report for Application No. 11190157.5 issued Jul. 6, 2012. (10 pages).

EP Search Report for Application No. 11190159.1 issued Feb. 21, 2012. (8 pages).

Extended European Search Report for Application No. 11190159.1 issued Jul. 6, 2012. (11 pages).

Extented European Search Report for Application No. 11195100.0 issued Oct. 17, 2012. (7 pages).

Extended European Search Report for Application No. 13166905.3 issued Aug. 13, 2013 (9 Pages).

Extended European Search Report for Application No. 13166907.9, issued Aug. 1, 2013 (6 pages).

Extended European Search Report for Application No. 13166908.7, issued Aug. 23, 2013 (8 pages).

Extended European Search Report for Application No. 13185425.9 issued Dec. 16, 2013 (9 Pages).

Extended European Search Report for Application No. 13199724.9 issued Apr. 4, 2014 (6 Pages).

Heller, Handbook of Biodegradable Polymers, edited by Domb, et al., Hardwood Academic Press, pp. 99-118 (1997).

International Search Report for Application No. PCT/US2011/067119, mailed Jun. 4, 2012. (6 pages).

Kemnitzer et al., Handbook of biodegradable Polymers. Eds. Domb et al. Hardwood Acad. Press. 1997;251-72.

Vandorpe et al., Handbook of Biodegradable Polymers, edited by Domb, et al., Hardwood Acad. Press, pp. 161-182 (1997).

Chinese Office Action for Application No. 201310163420.7, issued May 5, 2016 (21 pages).

Japanese Office Action for Application No. 2011-281088, issued Nov. 10, 2015 (4 pages).

Chinese Office Action for Application No. 201310163700.8 issued Jun. 3, 2016 (14 pages).

U.S. Appl. No. 15/264,645, filed Sep. 14, 2016, Surgical Filament Snare Assemblies.

Chinese Office Action for Application No. 201310429109.2 dated Oct. 24, 2016 (13 pages).

Chinese Office Action for Application No. 201310741440.8, dated Jan. 26, 2017 (12 pages).

* cited by examiner

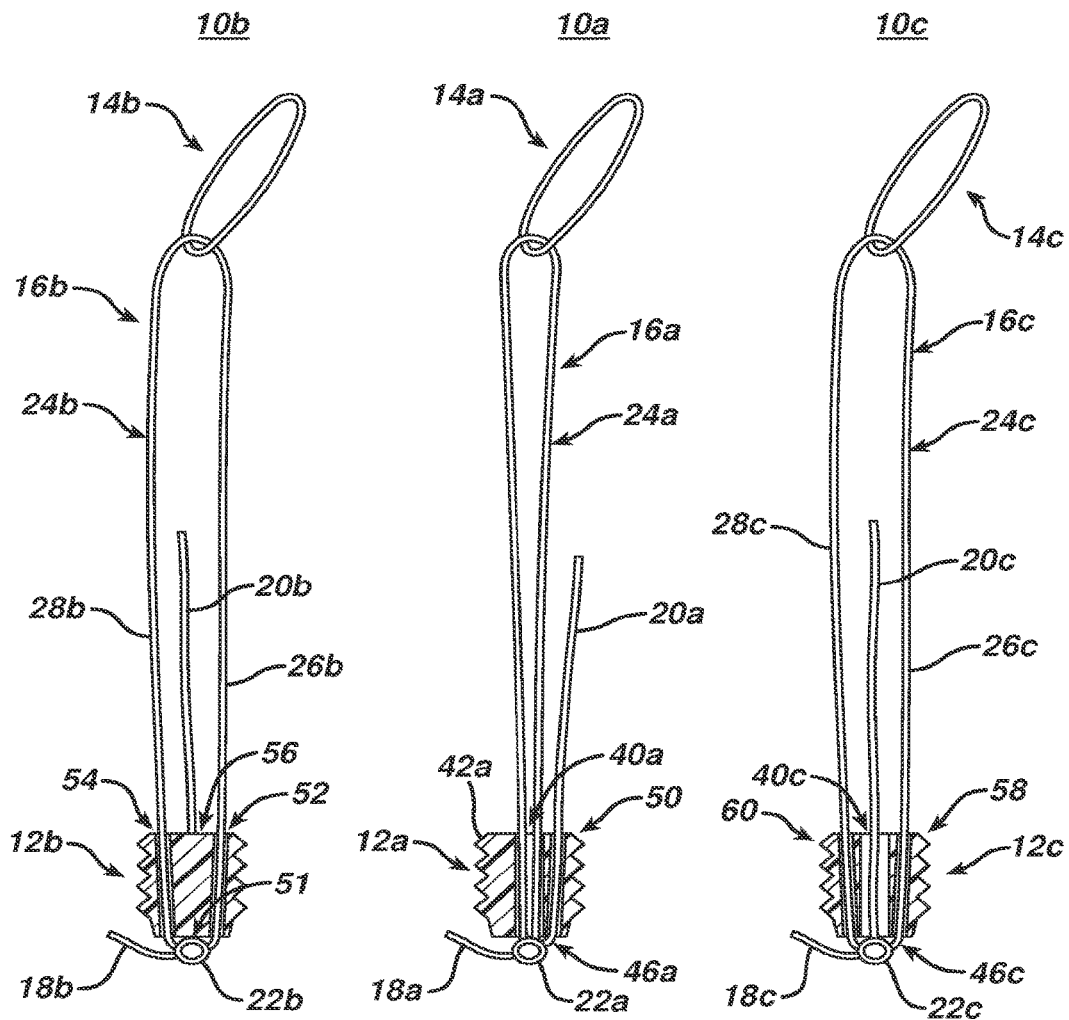

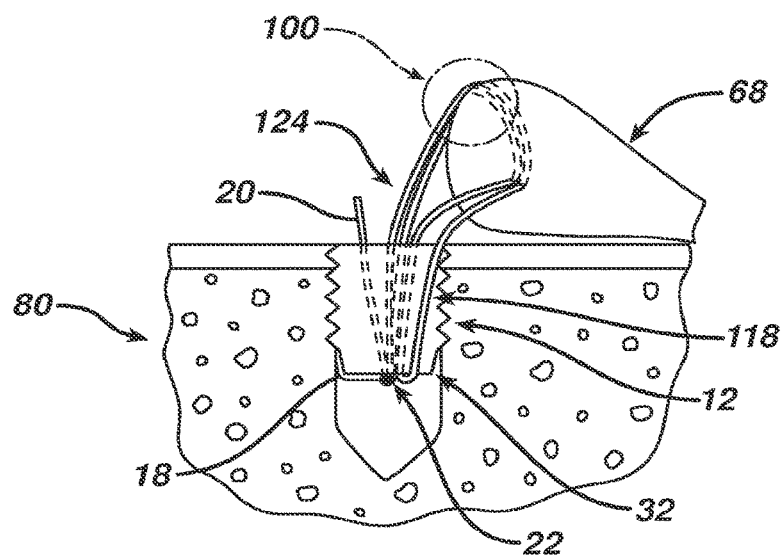
FIG. 8A
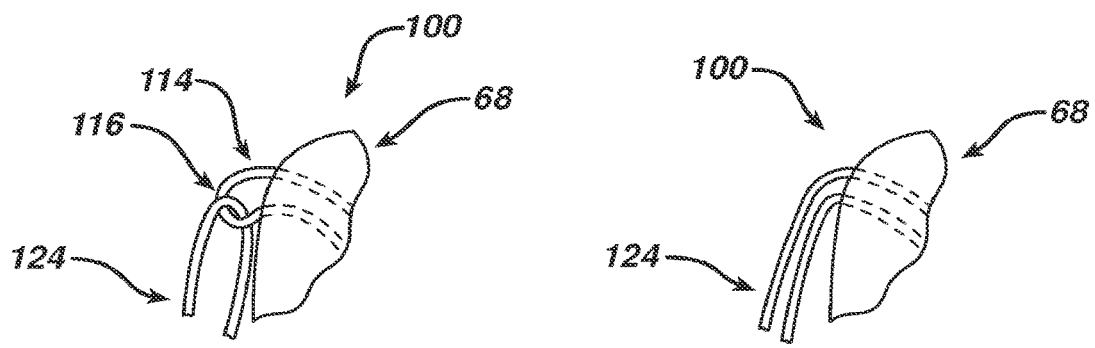
FIG. 8B  FIG. 8C

ADJUSTABLE ANCHOR SYSTEMS AND METHODS

1. BACKGROUND

The present application is a divisional of and claims priority to U.S. patent application Ser. No. 13/336,151, filed on Dec. 23, 2011, and entitled "Adjustable Anchor Systems and Methods," which is a continuation-in-part of U.S. patent application Ser. No. 12/977,146, filed on Dec. 23, 2010, and entitled "Adjustable Anchor Systems and Methods," and which issued as U.S. Pat. No. 8,821,543 on Sep. 2, 2014, each of which is hereby incorporated by reference in its entirety.

2. FIELD

The invention relates to a system and method for securing tissue to bone and more particularly to adjustable tensioning of tissue which eliminates the need for knot-tying by a user.

3. DESCRIPTION OF THE RELATED ART

A common injury, especially among athletes, is the complete or partial detachment of tendons, ligaments or other soft tissues from bone. Tissue detachment may occur during a fall, by overexertion, or for a variety of other reasons. Surgical intervention is often needed, particularly when tissue is completely detached from its associated bone. Currently available devices for tissue attachment include screws, staples, suture anchors and tacks. An example of a cannulated suture anchor is provided in U.S. Patent Application Publication No. 2008/0147063 by Cauldwell et al.

There are a number of suture implant systems which proclaim to be "knotless", that is, to not require a surgeon to tie a knot during surgery. Many such systems control tension on tissue by the depth to which an anchor is driven into bone. U.S. Pat. Nos. 5,782,864 and 7,381,213 by Lizardi disclose certain types of suture anchors which capture a fixed-length loop of suture. Adjustable loop knotless anchor assemblies utilizing an anchor element inserted into a sleeve are described by Thal in U.S. Pat. Nos. 5,569,306 and 6,045,574 and in U.S. Patent Application Publication No. 2009/0138042.

Suture anchor systems with sliding knots for repairing torn or damaged tissue, especially for meniscal repair, are disclosed in U.S. Pat. No. 7,390,332 by Selvitelli et al. and are utilized in the OmniSpan™ meniscal repair system commercially available from DePuy Mitek Inc., 325 Paramount Drive, Raynham, Mass. 02767. Other suture anchor systems with sliding and locking knots for repairing tissue include U.S. Pat. No. 6,767,037 by Wenstrom, Jr.

It is therefore desirable to adjust tension on a tissue after an anchor has been fixated in bone without requiring a surgeon to tie any knots, especially during arthroscopic procedures.

4. SUMMARY

A suture anchor system according to the present invention comprises a suture anchor, a collapsible suture loop affixed to the anchor and a tissue suture attached to the collapsible suture loop.

In one aspect of the invention, the tissue suture is looped through the collapsible loop. The tissue suture can be formed from a separate piece of suture than the collapsible loop or from the same piece of suture from which is formed the collapsible loop. In one aspect of the invention, the tissue suture has a characteristic selected from the list of: materials, construction, size, and coatings which differs from such same characteristic of the collapsible loop. For instance the tissue suture can be adapted to be gentle to the tissue and the collapsible loop could be formed from a suture which slides more easily, has high strength, cinches well into a knot or other such characteristic which is not as important to the tissue suture. Preferably, the collapsible suture loop has a lower coefficient of friction than the tissue suture.

Preferably, the collapsible suture loop comprises a sliding knot through which a portion of the suture loop may be drawn to collapse itself. Preferably, the sliding knot comprises a fixed tail and a post limb. In aspect of the invention, the tissue suture comprises the fixed tail.

Preferably, an attachment member on the anchor passes through the collapsible suture loop to affix the collapsible loop to the anchor.

Preferably, the anchor has a central axial cannulation, the collapsible loop comprises a sliding knot which has a post limb extending from the sliding knot wherein tension upon the post limb collapses the loop and the collapsible loop and the post limb extend proximally out of the cannulation. Preferably a post in the anchor passes through the collapsible loop wherein to affix the collapsible loop to the anchor. In one aspect of the invention, the sliding knot is disposed distal of the post. Then, preferably, the post limb passes around a retaining surface adjacent to where the post passes through the collapsible loop and then passes proximally out of the cannulation. In such configuration the sliding knot is disposed proximal of the post. In another aspect of the invention, the tissue suture comprises the fixed tail.

Preferably, bone engaging protrusions are provided about the suture anchor. Preferably, the anchor has an elongated cylindrical shape whereby to be fixedly received within a hole drilled into a bone. Also preferably, the suture anchor, collapsible loop and tissue suture are sterile and packaged in a bacteria proof enclosure, also preferably with instructions for their use in attaching soft tissue to bone as described herein.

In one aspect of the invention a suture receiver is provided on the suture anchor for receiving the tissue suture. The suture receiver can comprise an eyelet at a distal end of the suture anchor. The eyelet can be formed of overlapping arms whereby to allow suture to be loaded into the eyelet between the arms. Alternatively, the eyelet is formed of a sidewall which has a funnel shaped slot therethrough to allow suture to be loaded into the eyelet through the slot. The suture receiver can comprise a notch at the distal end of the anchor, the notch being separate from the collapsible loop such that tissue suture in the notch does not abut any moving portion of the collapsible loop. The suture receiver helps guide the tissue suture along an exterior of the suture anchor as it is being implanted into a bone to trap the tissue suture between the anchor and the bone.

In one aspect of the invention, the anchor has a central axial cannulation and a suture grasper is received through the cannulation whereby to facilitate threading the tissue suture through the cannulation after it is loaded into a soft tissue. The suture grasper preferably comprises an elongated body passing through the cannulation with a suture capture mechanism distal of the suture anchor. The suture capture mechanism can be a loop of flexible material through which the tissue suture can be threaded.

A method according to the present invention provides for attaching a soft tissue to a bone. The method comprises the steps of: passing a tissue suture through a piece of soft tissue; implanting the suture anchor into the bone; and collapsing a collapsible suture loop that is affixed to the anchor and connected to the tissue suture and thereby tensioning the tissue suture. Preferably, slack in the tissue suture is removed prior to the step of implanting the suture anchor into the bone.

In one aspect of the invention the method comprises the step of trapping a first portion of the tissue suture between the suture anchor and the bone. A second portion of the tissue suture, adjacent the first portion of the tissue suture, can be passed through an axial cannulation through the suture anchor prior to implanting the anchor into the bone. This aids in aligning the tissue suture along the suture anchor as it is implanted to better trap the tissue suture. The second portion can be threaded through the cannulation via a suture grasper passed through the cannulation by loading the second portion into a suture capture mechanism of the suture grasper located distal of the anchor and then pulling the suture grasper, including the suture capture mechanism, proximally through the cannulation. Preferably, when the suture is trapped between the suture anchor and the bone, the soft tissue is disposed on the tissue suture between the first portion and where the tissue suture connects to the collapsible loop.

In one aspect of the invention, the tissue suture is engaged at a distal end of the suture anchor prior to implanting the anchor into the bone. Preferably, the tissue suture is loaded into an eyelet located at the distal end of the anchor.

Preferably, the collapsible loop is restrained via a post affixed to the suture anchor and passing through the collapsible loop. Preferably, the collapsible loop comprises a noose having a loop portion, a sliding knot closing the loop portion and a post limb extending out of the sliding knot and thus the step of collapsing the collapsible loop comprises applying tension to the post limb. In one aspect of the invention, the anchor comprises a central axial cannulation with the loop portion and the post limb extending proximally thereout and wherein the step of collapsing the loop draws the loop distally into the cannulation.

In one aspect of the invention, the tissue suture extends from the soft tissue as a loop which interconnects with the collapsible loop and thus the step of collapsing the collapsible loop tensions the loop of tissue suture.

In one aspect of the invention, the anchor comprises a central axial cannulation with a fixed tail of the sliding knot and the post limb extending proximally thereout and wherein the fixed tail is passed through the soft tissue to become the tissue suture.

5. BRIEF DESCRIPTION OF THE DRAWINGS

In what follows, preferred embodiments of the invention are explained in more detail with reference to the drawings, in which:

FIGS. 1A, 2 and 3 are schematic cross-sectional views of alternative anchor systems according to the present invention;

FIGS. 8A-8C show yet other embodiments in which the closed loop has a sufficient length to extend from the anchor up to and through the tissue, as illustrated in enlarged view in FIG. 8B, and another, less-preferred embodiment in which the closed loop has been eliminated and the adjustable loop passes completely through tissue as illustrated in FIG. 8C;

6. DETAILED DESCRIPTION OF THE PRESENTLY PREFERRED EMBODIMENTS

This invention may be accomplished by an adjustable anchor system for securing tissue to bone, including an anchor having at least one passage extending from a proximal end toward a distal end. The passage defines a restriction such as a restricted opening or an occluding element. The anchor has at least one bone-engaging feature disposed between the proximal and distal ends. The system further includes a first material, such as a first suture, formed as a closed, preferably fixed-length loop and capable of being placed through a portion of the tissue, and a second filament having a terminal end, a post limb and a sliding knot tied between the terminal end and the post limb to establish an elongated, adjustable-length loop which extends beyond the proximal end of the anchor and captures the closed loop of the first material. The knot of the second filament is restrained by the restricted opening or occluding element when tension is applied as desired to the post limb to shorten the elongated loop to draw the tissue toward the anchor until a desired tension is achieved.

Figure 1:
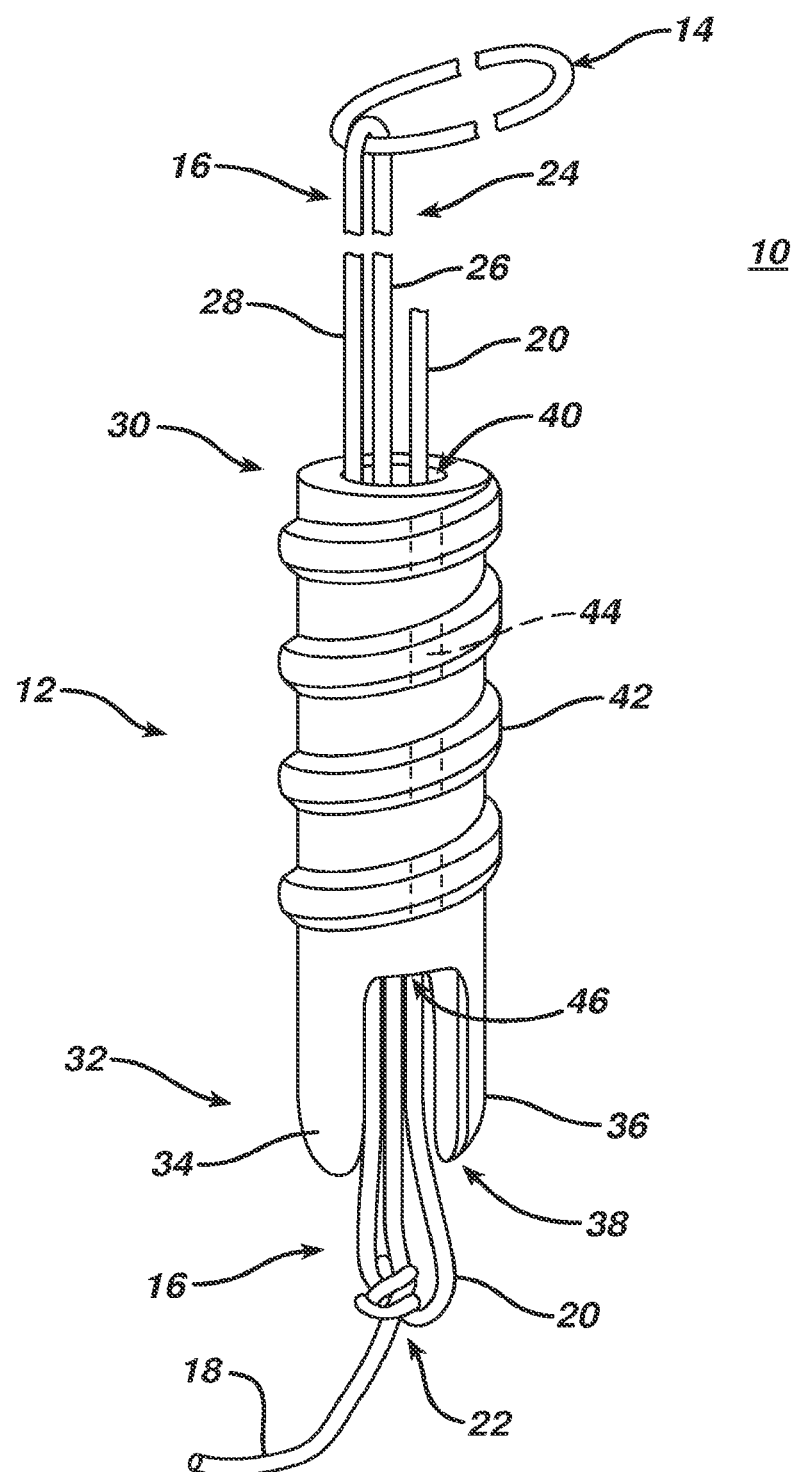
FIG. 1 is a perspective view of an adjustable anchor system according to the present invention having a closed loop and an adjustable loop of filament.

Adjustable anchor system 10, FIG. 1, has a suture anchor 12, a closed, fixed-length loop 14 of a first material, and a second filament 16 having a terminal end 18, a post limb 20, a sliding bunt line half hitch knot 22, and an adjustable loop 24 with loop limbs 26 and 28. In one construction, suture anchor 12 is similar to the cannulated suture anchor disclosed by Cauldwell et al. in U.S. Patent Application Publication No. 2008/0147063, incorporated herein by reference. In anchor systems according to the present invention, however, it is not necessary to have a post-like suture-engaging member or other occluding element over which one or more sutures or suture limbs pass to serve as a restriction to proximal movement; in many constructions, it is sufficient to have a restricted opening 46 to prevent withdrawal of knot 22 as discussed in more detail below, particularly in relation to FIGS. 1A-3.

Suture anchor 12 has a proximal end 30 and a distal end 32 with opposed distal arms 34 and 36 defining cut-out 38 between them. Passage 40 is an inner lumen which runs from proximal end 30 to distal cut-out 38. Although knot 22 is shown extending beyond cut-out 38 in FIG. 1 for purposes of illustration, knot 22 preferably is seated against restricted opening 46 between arms 34 and 36, or otherwise maintained at the distal end 32 by a cavity or other feature, during insertion of anchor system 10 into a patient to minimize interference by the knot 22 with the bone-engaging feature 42, or other exterior surface of anchor 12, and the bone in which suture anchor 12 is fixated.

One or more bone-engaging features 42, such as the helical thread illustrated in FIG. 1 or other features such as teeth, ridges, or other protrusions, are formed on the exterior of anchor 12 to enhance fixation in bone. In one construction, the suture anchor rotates to toggle into bone at its proximal end to minimize withdrawal. In a number of constructions, a hole is formed in bone prior to anchor insertion; in other constructions, a suture anchor is inserted directly into bone.

One or more passages or channels may be formed on the exterior of the suture anchor, such as channel 44 illustrated in phantom, FIG. 1, traversing bone-engaging element 42. Other configurations are illustrated in FIGS. 1A, 2 and 3 for adjustable anchor systems 10a, 10b and 10c, respectively, according to the present invention, having first, fixed-length loops 14a, 14b, 14c and second, adjustable length filaments 16a, 16b, 16c, respectively. Anchor 12a, FIG. 1A, defines an inner lumen 40a and an external passage 50 extending from the distal end to the proximal end of anchor 12a. Sliding knot 22a, formed in second filament 16a, is seated against restricted opening 46a, adjustable loop 24a extends through passage 40a to capture closed loop 14a, and post limb 20a lies within external channel 50 in this construction.

It is a matter of surgeon preference whether a terminal end, such as terminal end 18a, FIG. 1A, is kept at a length sufficient to lie against the exterior of at least one bone-engaging feature 42a to be trapped against bone during insertion, or is trimmed to a shorter length. Different examples of terminal end length are provided in FIGS. 6-8 below. Further, a restriction such as restricted opening 46a may be defined at least in part by engagement with bone when anchor 12a is fixated in bone to prevent knot 22a from moving with post limb 20a when tension is applied to post limb 20a as described in more detail below for procedures of using an anchor system according to the present invention.

Anchor system 10b, FIG. 2, has at least three external passages or channels 52, 54 and 56 without any internal passages in this construction. Knot 22b is maintained at the distal end of anchor 12b by occlusion 51, defined at least in part by the distal surface of anchor 12b, while limbs 26b, 28b of loop 24b lie within passages 52, 54 and post limb 20b of second filament 16b lies within passage 56. As described above, occlusion 51 may be defined in part by engagement of anchor 12b with bone after fixation.

Anchor system 10c, FIG. 3, has an internal passage 40c through which post limb 20c extends from a restricted opening 46c which holds knot 22c. External passages 58, 60 carry limbs 26c, 28c of adjustable loop 16c. Although anchors 12a, 12b and 12c are shown without distal-extending arms in those constructions, in other constructions one or more such distal extensions or other protrusions are provided, similar in some constructions to Cauldwell et al. cited above or to U.S. Pat. No. 7,381,213 by Lizardi, also incorporated herein by reference. In yet other constructions, a cylindrical or otherwise circumferential cavity, bowl or countersink feature is provided at the distal end of the anchor to seat the knot 22 during insertion and fixation.

In preferred constructions, loop 14, also referred to as a first filament, and second filament 16 are formed of one or more types of sutures. Acceptable diameters for second filament 16 include size 0 or size 2 suture, such as Orthocord™ suture commercially available from DePuy Mitek, while the same or larger diameters such as size 2 to size 5 suture are preferred for loop 14, such as Ethibond™ suture available from Ethicon. Orthocord™ suture is approximately fifty-five to sixty-five percent PDS™ polydioxanone, which is bioabsorbable, and the remaining percent ultra high molecular weight polyethylene, while Ethibond™ suture is primarily high strength polyester. In some constructions, especially for shoulder repair procedures, loop 14 has a fixed length of approximately one inch while adjustable loop 24 has a length of at least eighteen inches. The amount and type of bioabsorbable material, if any, utilized in the first or second filament is primarily a matter of surgeon preference for the particular surgical procedure to be performed.

While the same type of suture can be used for both loop 14 and filament 16, a suture having a lower abrasive property at its surface is preferred for the first material forming closed loop 14. The lower abrasive property can be achieved by a larger diameter, a softer composition, a softer braid, plait or strand pattern, or a combination of such characteristics. In some constructions, the suture material for closed loop 14 is tied with a fixed knot to form the fixed-length loop 14. In other constructions, loop 14 is molded or otherwise formed as a ring of material.

Slidable knot 22 has been described as a bunt line half hitch knot in some constructions, but other suitable knots will be readily apparent to those of ordinary skill in the suture tying art after reviewing the present invention. The term "slidable" as used herein is intended to include slidable, lockable knots as well as slidable knots. Several types of suitable knots are described in the Arthroscopic Knot Tying Manual (2005) available from DePuy Mitek, as well as in U.S. Pat. No. 6,767,037 by Wenstrom, Jr.

One procedure according to the present invention for utilizing a cannulated anchor system similar to that shown in FIG. 1 is illustrated in FIGS. 4-7 for attaching tissue 68 to bone 80. Reference numerals utilized to describe the system shown for this procedure follow the numerals utilized for system 10, FIG. 1, for simplicity and clarity, although a number of other types of anchors with different filament limb arrangements as illustrated in other Figures could also be utilized in a similar manner. An initial suture 70, FIG. 4, having a needle 72 at its distal end is passed through tissue 68 to draw at least closed loop 14 at least partially through tissue 68. Alternatively, a suture passing instrument is inserted through tissue 68 to grasp the closed loop 14 and pull it through the tissue 68. The extent to which elongated, adjustable loop 24 is drawn through tissue 68, and whether an anchor passes through or engages the closed loop 14 or adjustable loop 24, are described in more detail below relative to FIGS. 8-8C.

Figure 4:
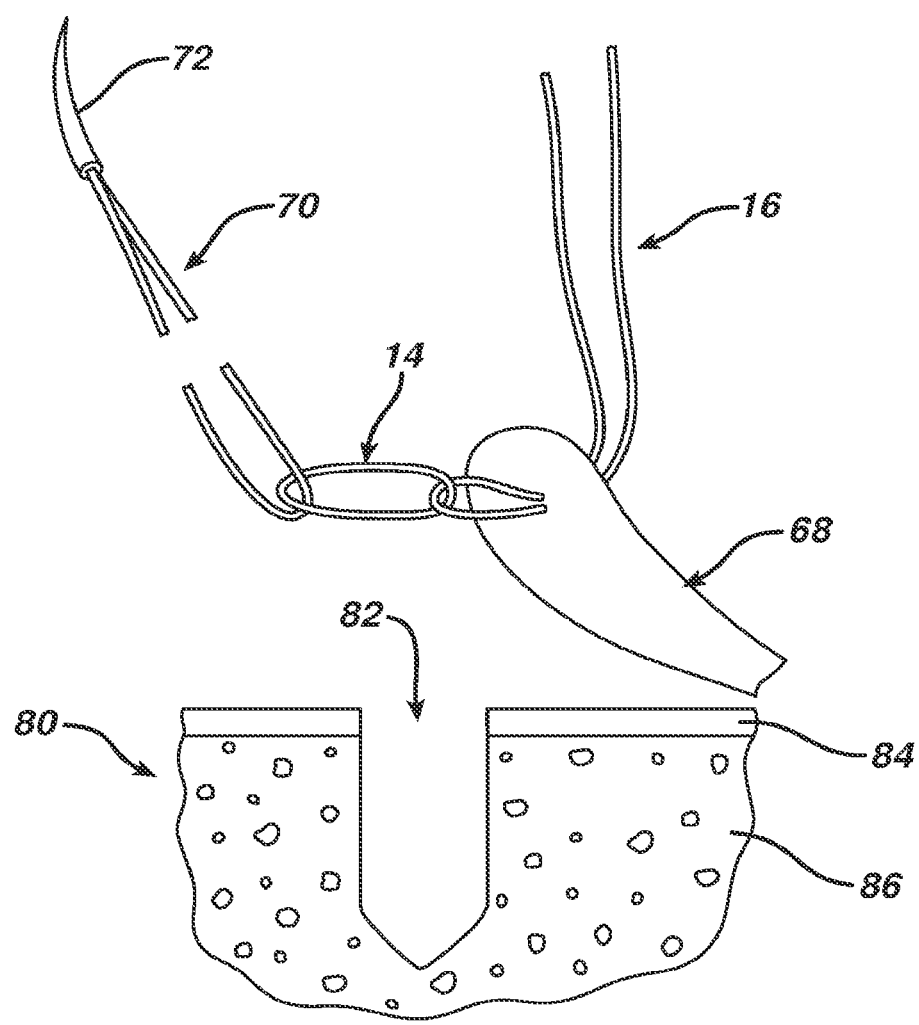
FIG. 4 is a schematic view of a closed loop after it has been pulled through a portion of tissue to be secured to bone, which may draw a portion of the adjustable loop with it through the tissue.
Figure 5:
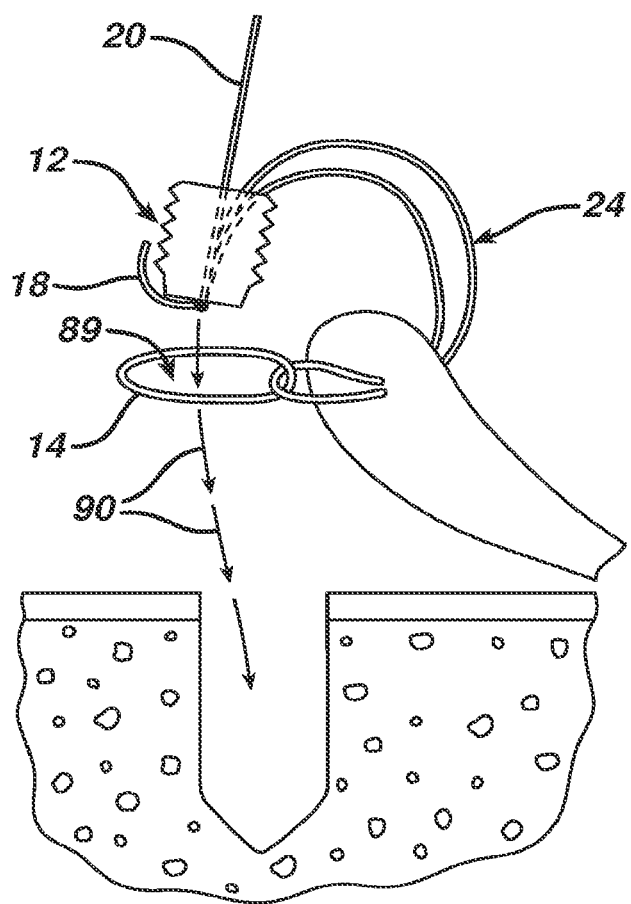
FIG. 5 illustrates an anchor being passed through the fixed loop and directed toward a hole formed in the bone.
Figure 6:
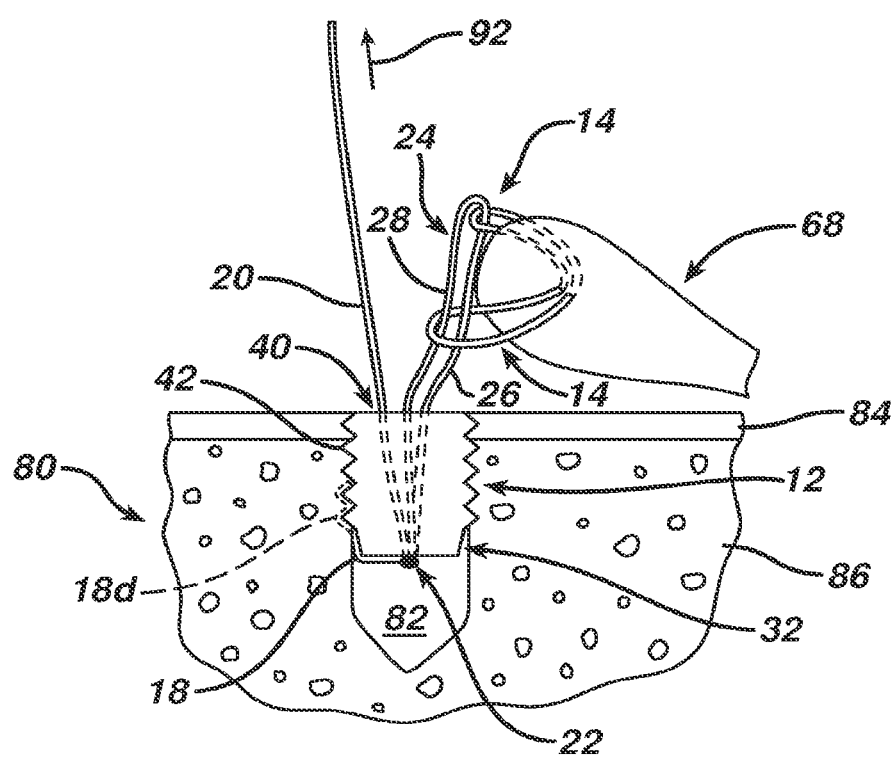
FIG. 6 shows the anchor fixated in bone with tension to be applied on the post limb.

In this procedure, a hole 82, FIG. 4, is formed through compact layer 84 into cancellous layer 86 of bone 80 at a desired repair location. Anchor 12, FIG. 5, is passed through an opening 89 in closed loop 14 as indicated by arrows 90 and is fixated in bone as shown in FIG. 6. Preferably, post limb 20 is extracted from the closed loop 14 after anchor 12 passes through the opening 89 in closed loop 14, FIG. 5, so that post limb 20 can pull directly one of adjustable loop limbs through the knot 22 without being constrained by closed loop 14. Terminal end 18 is trapped between bone 86 and a portion of distal end 32 of anchor 12 in this construction, and sliding knot 22 is held by a restricted opening in internal lumen 40. Alternatively, terminal end 18 has a sufficient length so that it extends proximally along the exterior of the anchor 12 past a plurality of bone engaging features 42 as illustrated in phantom as length 18d, or is a shorter length 18e as shown in FIG. 8.

Figure 7:
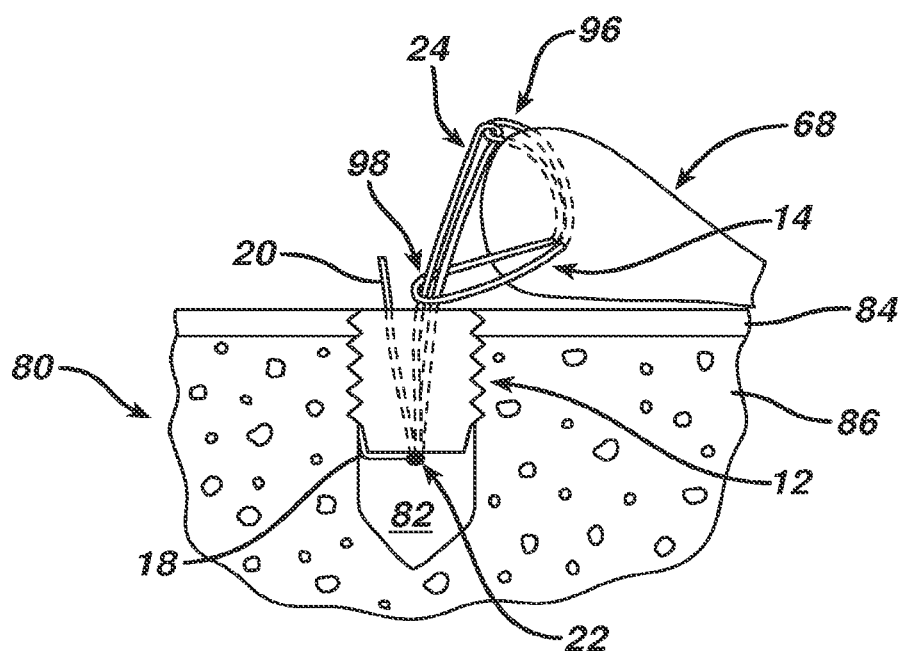
FIG. 7 illustrates the tissue in a desired position under final tension after the post limb has been trimmed.

After fixation of anchor 12, FIG. 6, proximal tension is applied to post limb 20 as indicated by arrow 92. As post limb 20 is moved proximally, adjustable loop 24 readily slides through closed loop 14 as limbs 26 and 28 are shortened. Tissue 68 is thereby drawn toward anchor 12 until a final desired position, under desired tension, is achieved as shown in FIG. 7. Closed loop 14 engages the elongated loop 24 at first and second locations 96 and 98.

Figure 8:
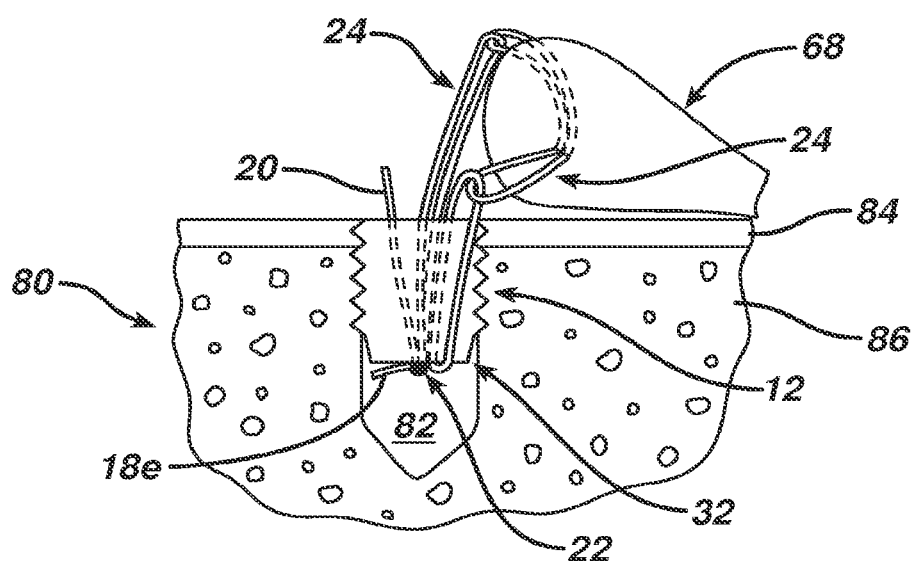
FIG. 8 shows an alternative technique to that illustrated in FIGS. 6 and 7 in which the anchor engages the closed loop instead of passing through it.

Other systems and methods according to the present invention are shown in FIGS. 8-8C as alternatives to the final configuration shown in FIG. 7. Terminal end 18e, FIG. 8, is intentionally short so that it is not trapped between the anchor 12 and bone 80. In this construction, terminal end 18e remains within the bone hole 82 and is not placed under tension of any type.

Figure 11A:
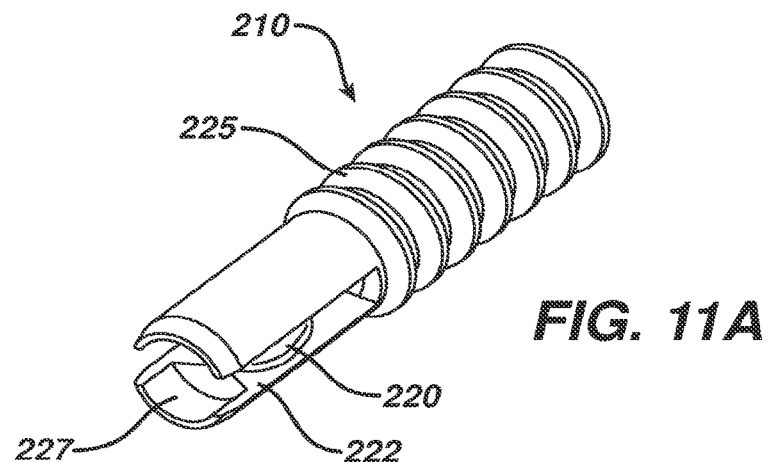
FIG. 11A is a perspective view of the suture anchor body of the suture anchor system of FIG. 10.
Figure 11B:
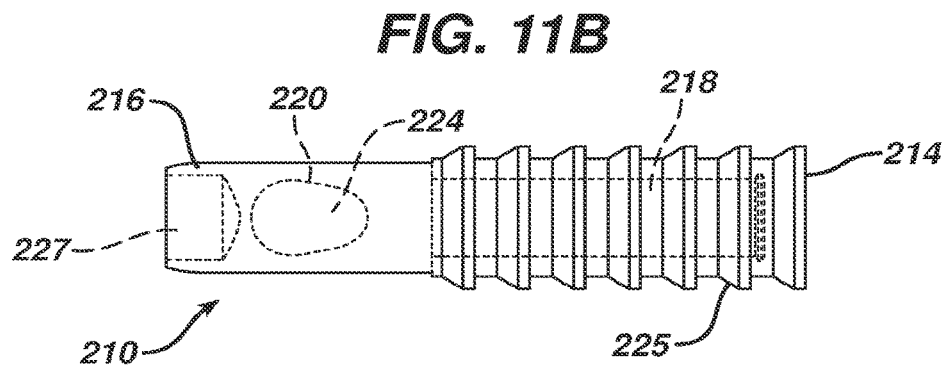
FIG. 11B is a top plan view of the suture anchor body of FIG. 11A.
Figure 11C:
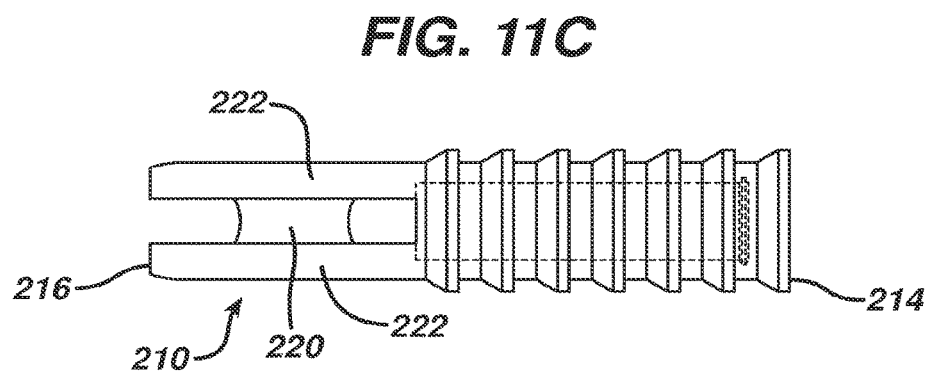
FIG. 11C is a side elevation view of the suture anchor body of FIG. 11A.
Figure 12:
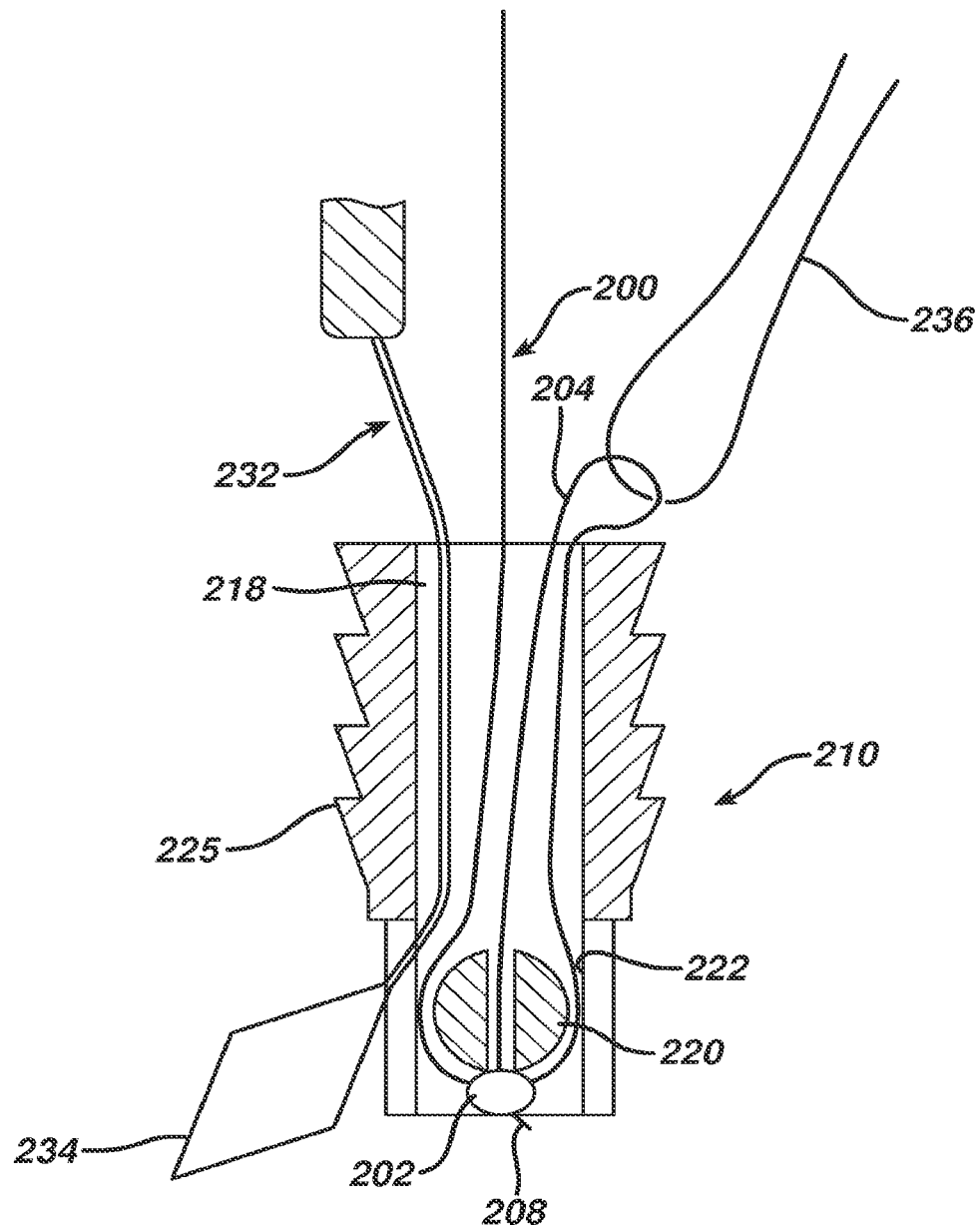
FIG. 12 is a front elevation view in cross-section of a further embodiment of a suture anchor system according to the present invention.

Instead of requiring an opening 89, FIG. 5, in closed loop 14 to be greater than the circumference of the anchor 12 so that anchor 12 can pass completely through the closed loop 14, in other constructions the distal end 32 engages a portion of the closed loop 14 as shown in FIG. 8. Filament engagement can be accomplished such as shown in FIGS. 11 and 12 of U.S. Pat. No. 7,381,213 by Lizardi. However, one benefit achieved by the present invention is that further tensioning of tissue 68 is possible after anchor fixation by pulling on the post limb of the adjustable loop. Another benefit of the present invention is that the anchor inserter or driver and related driver instruments are removed prior to final tensioning and positioning of the tissue to be repaired to provide improved visual and tactile feedback to the surgeon.

Other arrangements of filaments are illustrated in FIGS. 8A-8C. Anchor 12, FIG. 8A, engages filament portion 118 which passes through tissue 68 to emerge at the other, proximal side in the circled region indicated at 100. In the construction shown in FIG. 8B for that circled region 100, adjustable loop 124 passes through a portion of closed loop 114. In other words, the same filament limbs form portions 114 and 118 of a single closed, fixed-length loop. This arrangement is preferred because the limbs of adjustable loop 124 are able to slide over the closed loop filament at location 116 without passing through tissue as adjustable loop 124 is reduced in size.

In contrast, limbs of adjustable portion 124 pass through tissue 68 in FIG. 8C, which represents an alternative configuration for FIG. 8A, and the adjustable limbs emerge to form portion 118 which is engaged by the distal end 32 of anchor 12. In other words, no closed loop is utilized in the configuration represented by FIG. 8C. However, eliminating the fixed-length loop is less desirable because the adjustable loop may tend to lock on itself, and may bind with or cause damage to the soft tissue through which it passes. The adjustable loop may be prone to locking on itself even if the anchor is passed completely through the adjustable loop. Further, adjustability of portion 118, FIG. 8C, may be further impeded by an interference fit with bone, unless the limbs of portion 118 are properly aligned in channels or other exterior passages along anchor 12.

Figure 9:
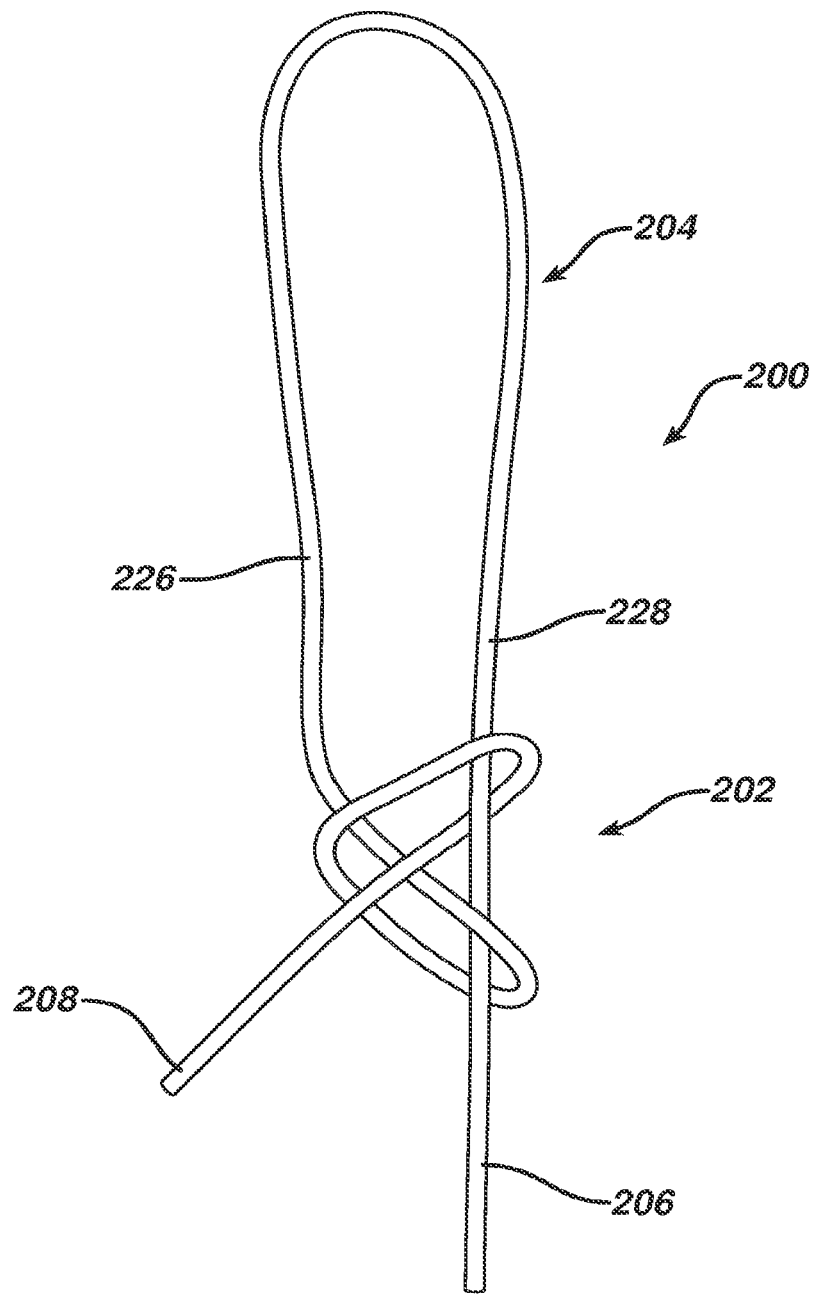
FIG. 9 is a top plan view of a Tennessee Slider knot for use with suture anchor systems according to the present invention.

A suture 200 for use with anchors according to the present invention can employ a Tennessee Slider knot 202 (FIG. 9) in substitution for the blunt line half hitch knot 22. It comprises a loop 204, post limb 206 and terminal end 208. The terminal end 208 passes over and then behind the post limb 206, then over the loop 204, and then finally behind the post limb 206 and back out.

FIGS. 10 and 11A to 11C illustrate a further embodiment of a suture anchor 210 according to the present invention. It comprises a body 212 having a proximal end 214 and distal end 216 with an axial lumen 218 passing through the proximal end 214. The distal end 216 is slotted with a saddle 220 between two distal sides 222. An aperture 224 passes axially through the saddle 220. Annular barbed flanges 225 about the body 212 provide for enhanced fixation.

The suture 200 with the Tennessee Slider knot 202 is positioned in the anchor 210 with the knot 202 distal of the aperture 224 in a pocket 227 created into the sides 222, a fixed tail 226 of the loop 204 passing proximally from the knot 202 through the aperture 224 and an adjustable tail 228 of the loop 204 wrapping around the saddle 220 to meet the knot 202. The loop 204 extends proximally out of the lumen 218. The post limb 206 extends proximally around the opposite side of the saddle 220 from the adjustable tail 228 and also extends proximally out of the lumen 218. The anchor 210 can be employed in a fashion similar to the aforementioned embodiments.

Figure 10:
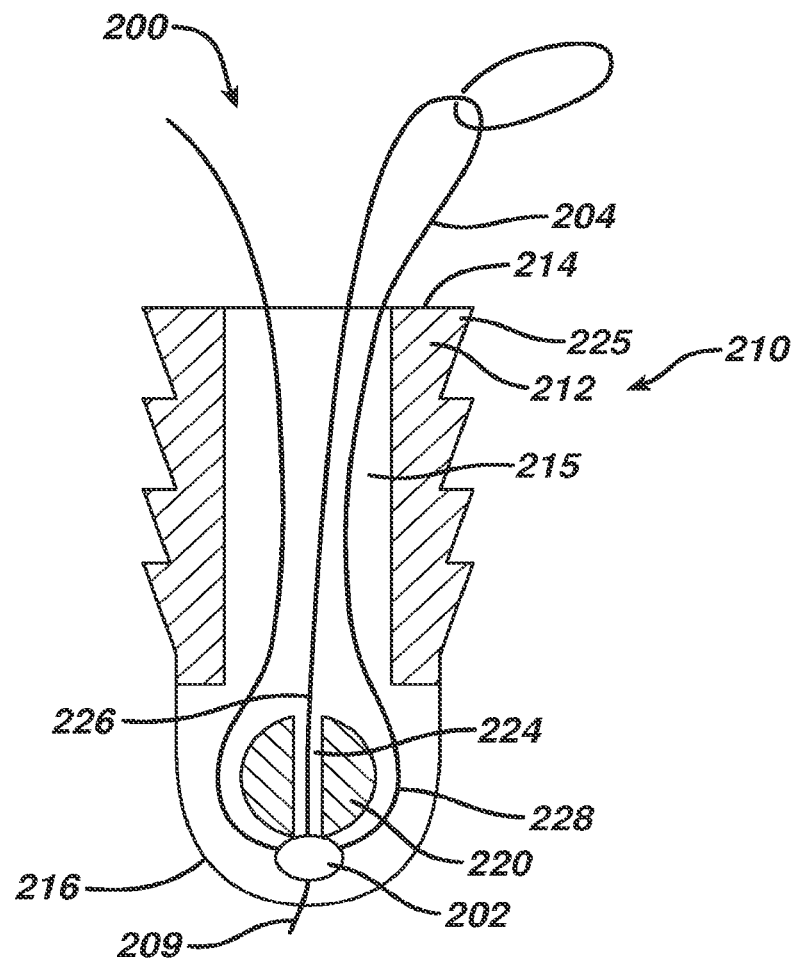
FIG. 10 is a front elevation view in cross-section of a further embodiment of a suture anchor system according to the present invention.

FIGS. 12 and 13A to 13G illustrate an alternative procedure for use with suture anchors according to the present invention. An anchor system 230 comprises the suture anchor 210 with suture 200 rigged as illustrated in FIG. 10 and with a flexible wire suture capture device 232 having a suture capture loop 234 (such as a Chia Percpasser available from DePuy Mitek, Inc. of Raynham, Mass.) threaded through the lumen 218 with the suture capture loop 234 distal of the anchor body 212. A separate length of tissue suture 236 is threaded through the loop 204.

Figure 13A:
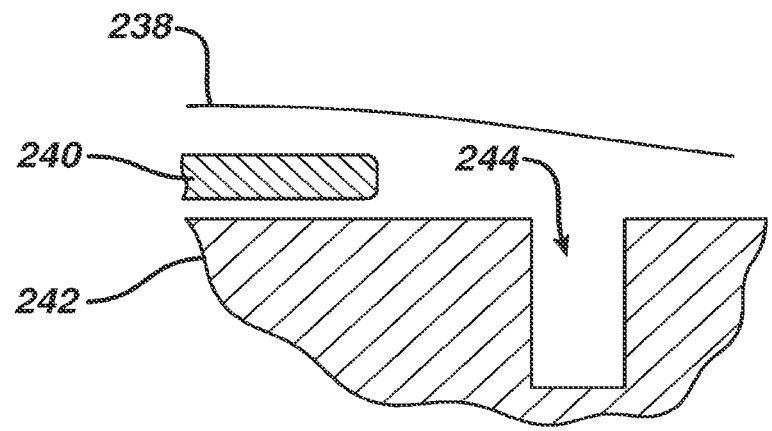
FIGS. 13A to 13H are front elevation views in cross-section of a method of using the suture anchor system of FIG. 12.
Figure 13B:
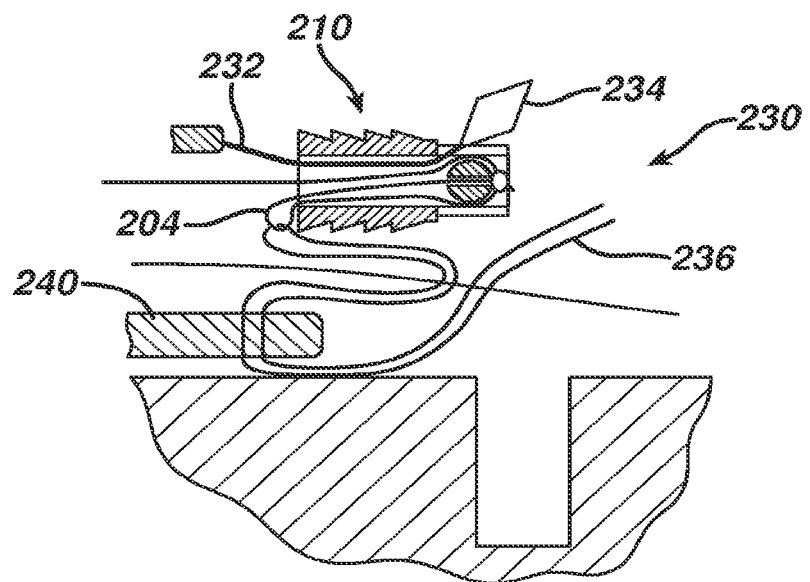
Figure 13C:
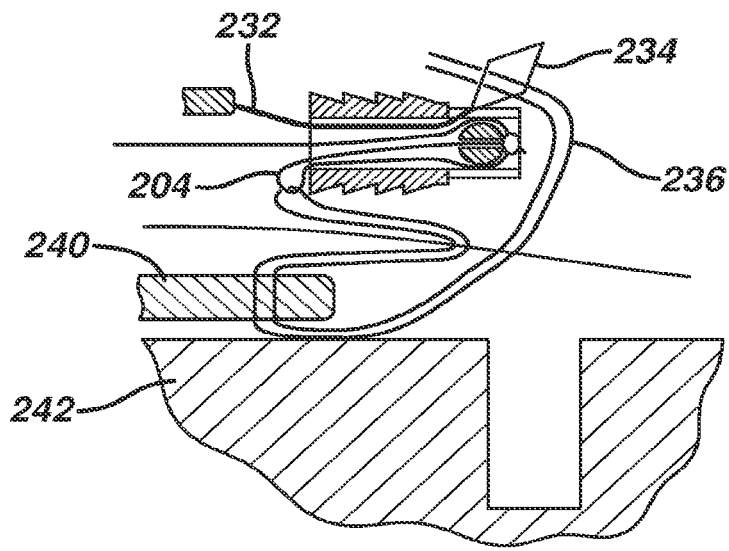
Figure 13D:
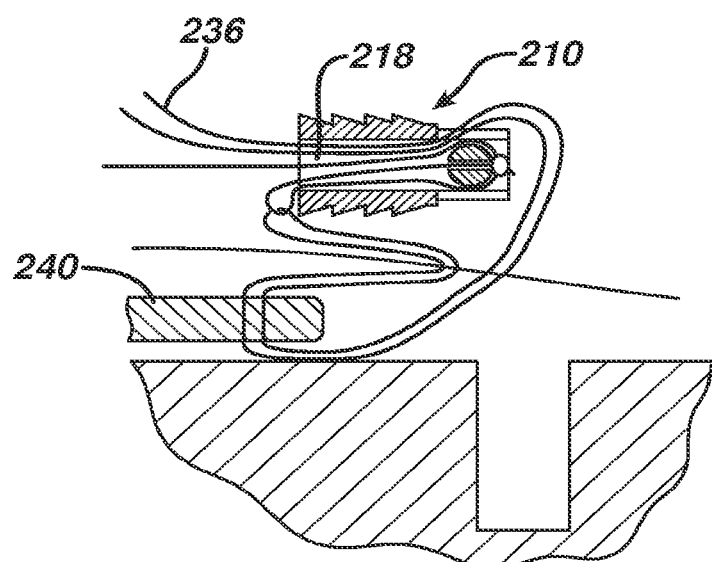
Figure 13E:
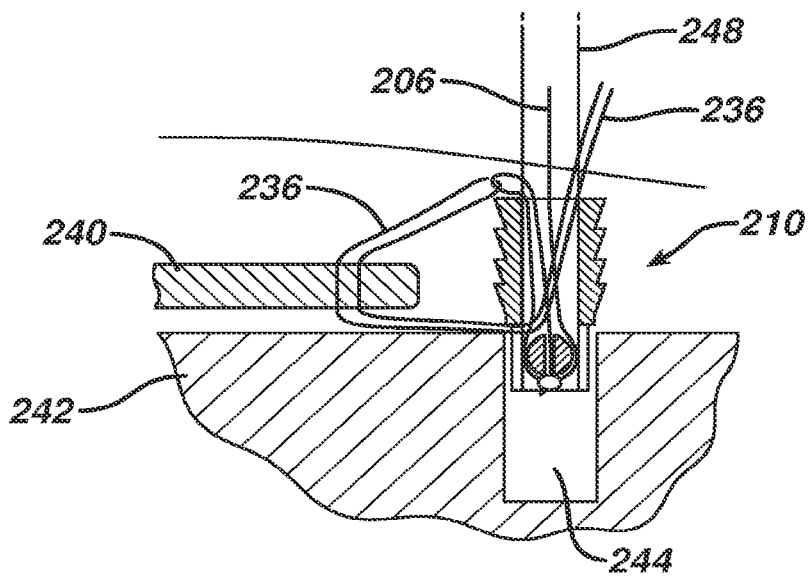
Figure 13F:
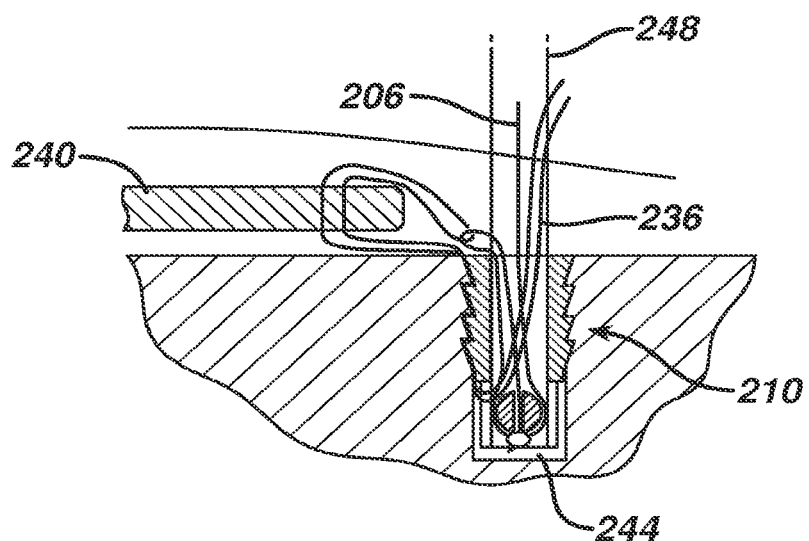
Figure 13G:
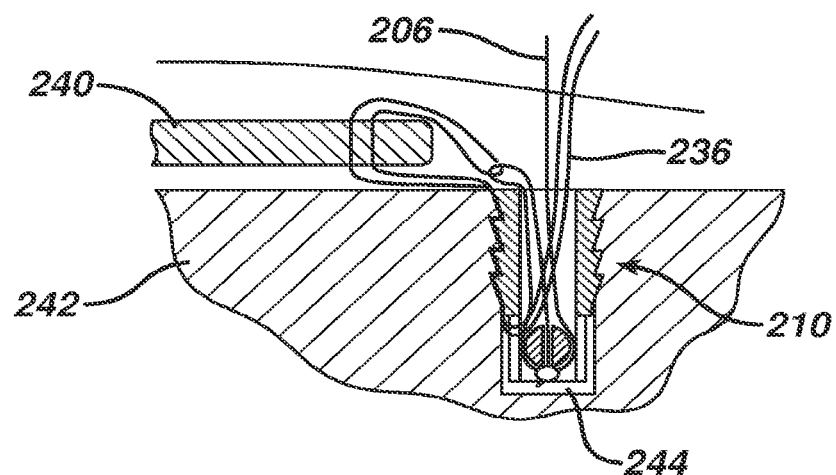
Figure 13H:
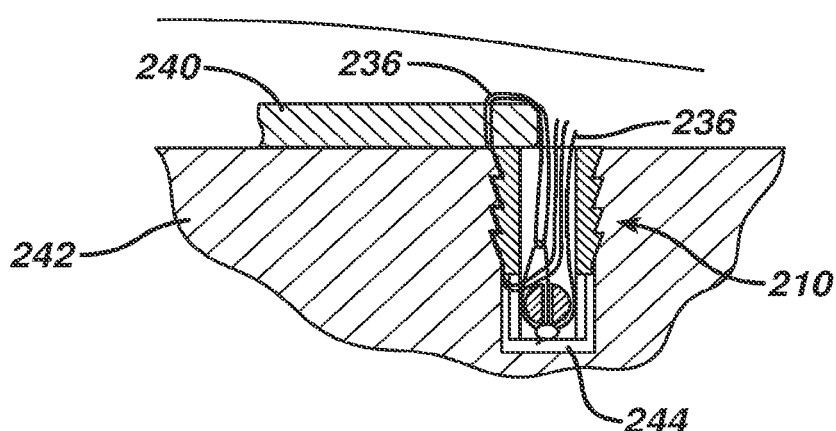

Typically the anchor system 230 is employed arthroscopically through a cannula which would pass through a patient's skin 238 to the tissue 240 and bone 242 where a repair is to be effected, but is not here illustrated to better focus on the rigging and motion of the sutures 200 and 236, and suture anchor 210. First a bone hole 244 is created adjacent the tissue 240 (FIG. 13A). The tissue suture 236 is passed through the tissue 240 (such as a rotator cuff tendon) and pulled back out of the cannula (not shown) to be outside of the skin 238 (FIG. 13B) where it can be threaded through the suture capture loop 234 (FIG. 13C). A suture passer for passing suture through tissue such as the EXPRESSEW Flexible Suture Passer available from DePuy Mitek, Inc. of Raynham, Mass. can be employed for this. The suture capture device 232 is pulled proximally out of the lumen 218 threading the tissue suture 236 through the lumen 218 (FIG. 13D). The suture anchor 210 is then passed down the cannula (not shown) to the bone hole 244. The suture anchor distal end 216 is placed into the hole 244 and slack is taken out of the tissue suture 236 (FIG. 13E). The anchor 210 is then driven into the bone hole 244 thus locking the tissue suture 236 between the anchor 210 and the bone 242 (FIG. 13F). Preferably the anchor 210 is inserted and driven into the bone hole 244 via a cannulated driver 248 with the post limb 206 situated within a cannulation 250 through the driver 248. After the anchor 210 is driven into the bone hole 244 the driver 248 is preferably removed (FIG. 13G) and then the post limb 206 is pulled to collapse the loop 204 and tension the tissue suture 236 (FIG. 13H).

Having the combination of the collapsible loop 204 and the tissue suture 236 provides great advantage while collapsing the loop 204 during tensioning of the repair. The loop 204 slides over the tissue suture 236 rather than sliding through the tissue itself which allows for easier tensioning of the repair as the coefficient of friction between the loop 204 and the tissue suture 236 will be less than if the loop 204 were sliding through the tissue itself and it minimizes any effects upon the tissue.

Although shown with a single anchor 210 a typical tissue repair might involve a row of anchors or multiple rows of anchors. The anchor 210 and other embodiments are for instance useful with dual row rotator cuff repairs in which a first medial row of anchors is placed beneath the cuff with suture threrefrom extending up through the cuff and running to a second lateral row of anchors located near the edge of the cuff. The suture extending up through the cuff from the medial row could replace the tissue suture 236 and be captured by anchors 210, in which case the suture capture device would preferably rigged through the lumen 218 as in FIG. 10 and then back through the loop 204 so that it would pass the suture from the medial anchors in place of the tissue suture 236. To facilitate loading such a loop of tissue suture the collapsing loop could be rigged with a closed loop such as loop 14 with the anchor being passed therethrough and through the tissue suture loop so that the collapsing loop rides against the closed loop as it collapses.

Figure 14:
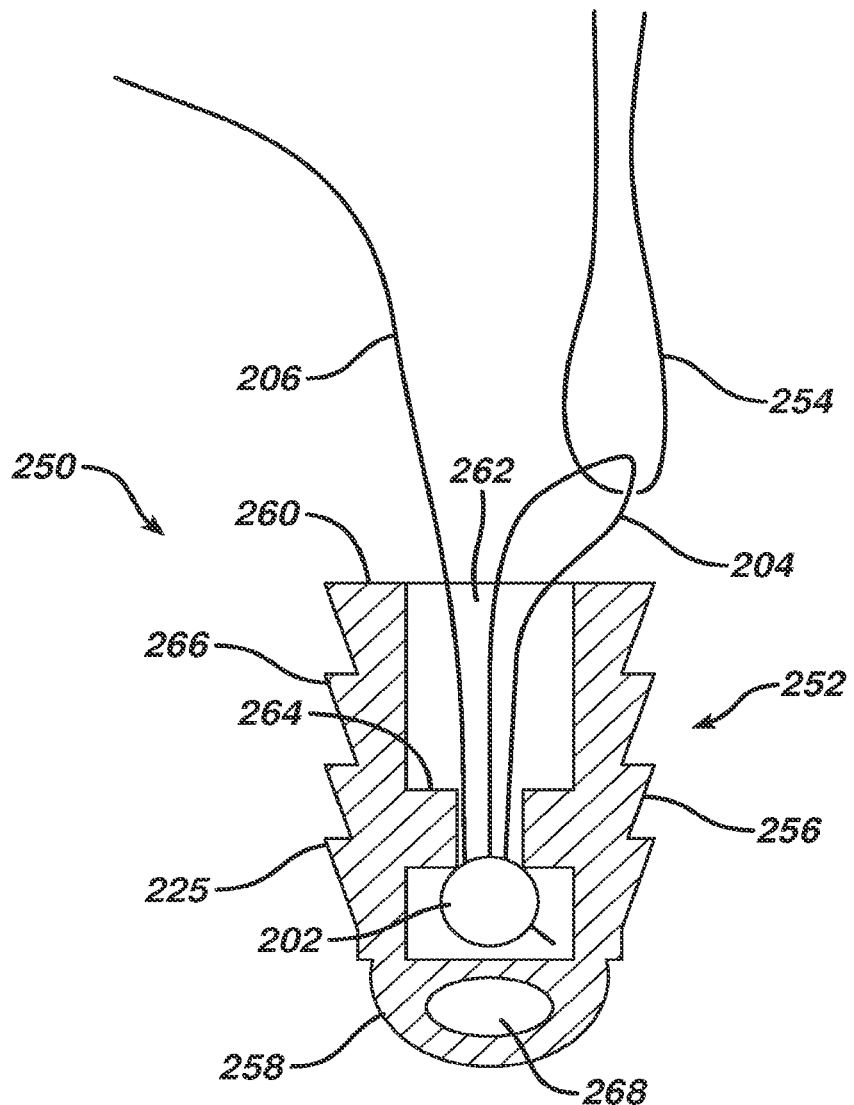
FIG. 14 is a front elevation view in cross-section of a further embodiment of a suture anchor system according to the present invention having a distal eyelet.

FIG. 14 illustrates a further embodiment of an anchor system 250 according to the present invention. It comprises a suture anchor 252 with suture 200 and a tissue suture 254. The anchor 252 comprises a body 256 having a distal end 258 and proximal end 260. An axial lumen 262 enters from the proximal end 260 and has a restriction 264 therein. Barbed flanges 266 encircle the body 256. An eyelet 268 is provided at the distal end 258. The suture 200 is situated in the anchor with the knot 202 distal of the restriction 264 and the loop 204 and post limb 206 passing proximally through the restriction 264 and out of the lumen 262. The restriction 264 restrains the knot 202.

Figure 15A:
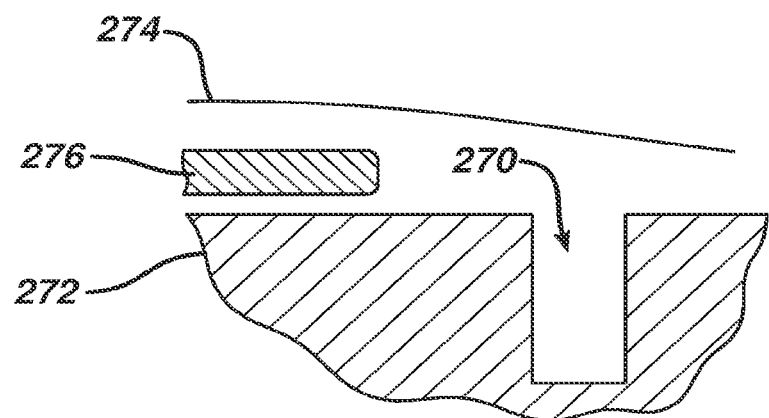
FIGS. 15A to 15E are front elevation views in cross-section of a method of using the suture anchor system of FIG. 14.
Figure 15B:
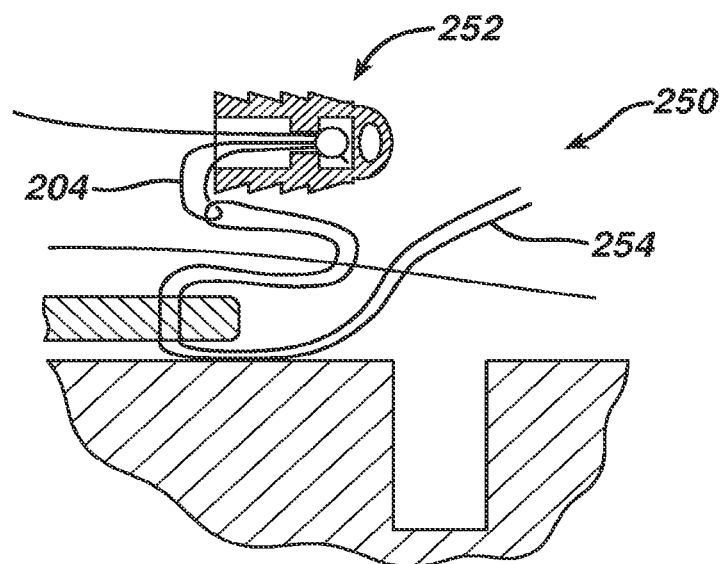
Figure 15C:
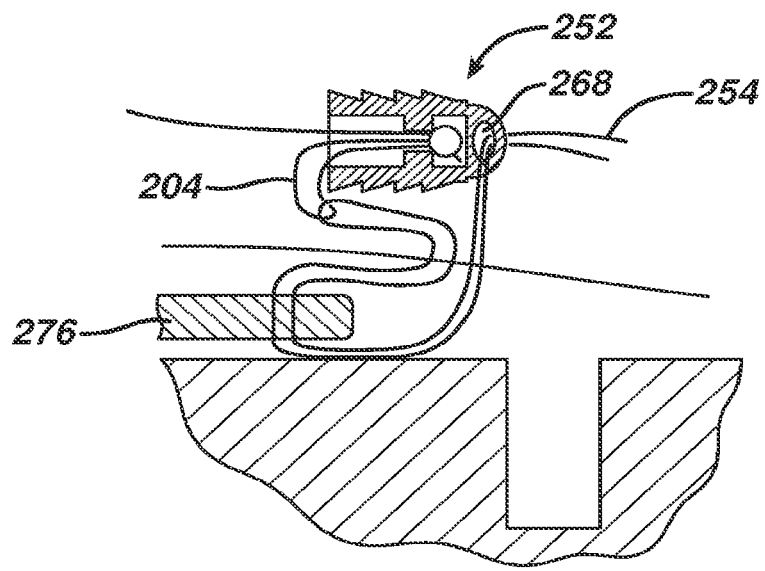
Figure 15D:
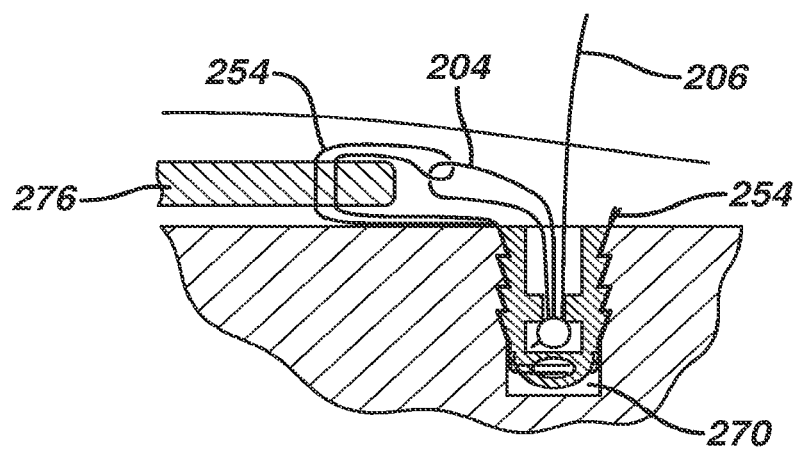
Figure 15E:
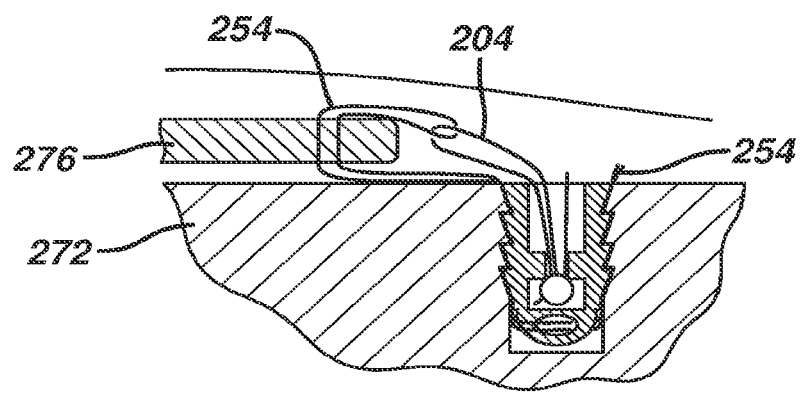

FIGS. 15A to 15E illustrate a procedure for the anchor system 250, and as in previous depictions the arthroscopy cannula and instrumentation are omitted for clarity. A bone hole 270 is formed in a bone 272 under a patient's skin 274 adjacent a tissue 276 (FIG. 15A). The tissue suture 254 is passed through the tissue (FIG. 15B) and passed through the eyelet 268 (FIG. 15C). A suture capture device 232 (not shown in FIGS. 15A TO 15E) could be employed through the eyelet 268 to ease loading the suture 254 therethrough. The anchor 252 is placed at the bone hole 270, the slack is removed from the tissue suture 254 and then the anchor is driven into the bone hole 270 to lock the tissue suture between the anchor 252 and the bone 272, preferably on two sides of the anchor 252. Tension applied to the post limb 206 collapses the loop 204 and tensions the tissue suture 254.

Figure 16A:
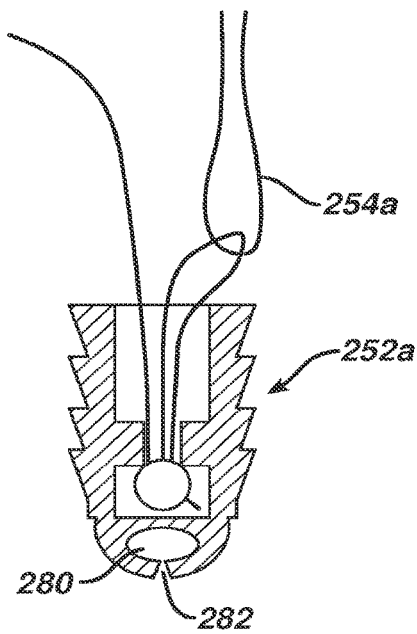
FIG. 16A is a front elevation view in cross-section of a further embodiment of a suture anchor system according to the present invention having a distal eyelet and having a funnel shaped opening into the eyelet for loading suture into the eyelet.
Figure 16B:
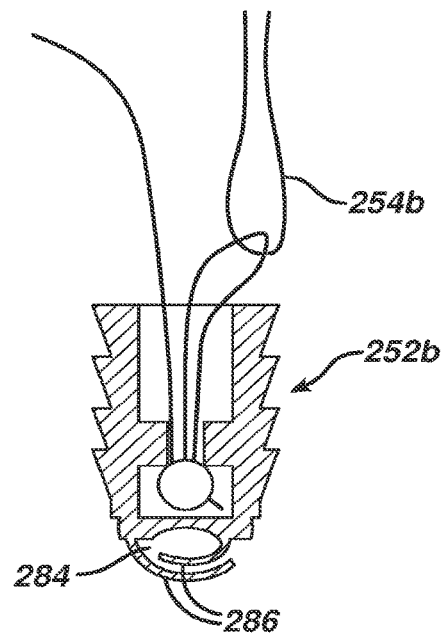
FIG. 16B is a front elevation view in cross-section of a further embodiment of a suture anchor system according to the present invention having a distal eyelet comprising overlapping arms for loading suture into the eyelet.
Figure 16C:
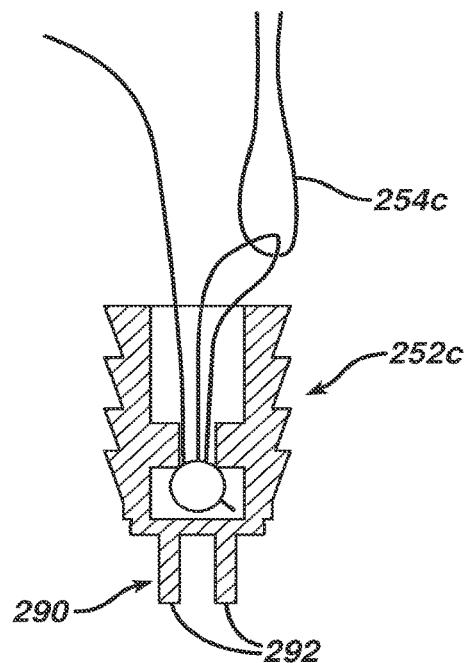
FIG. 16C is a front elevation view in cross-section of a further embodiment of a suture anchor system according to the present invention having a forked distal tip for receiving suture.
Figure 17:
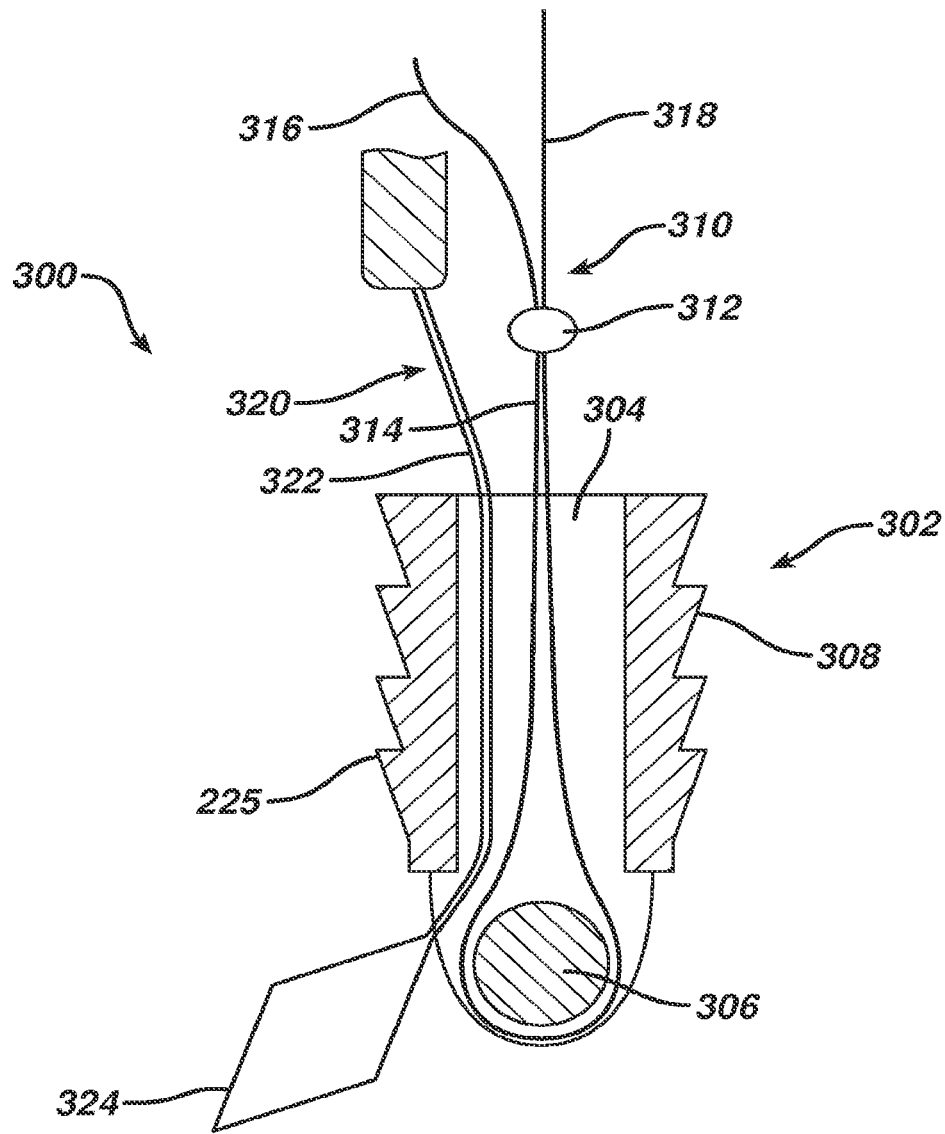
FIG. 17 is a front elevation view in cross-section of a further embodiment of a suture anchor system according to the present invention in which the sliding knot is proximal of the loop attachment to the anchor.

FIGS. 16A to 16C illustrate variations of the suture anchor system 250. Like parts in anchors 252a, 252b and 252c have like part numbers to the anchor 250 with the exception of their subscripts. Anchor 252a (FIG. 16A) has an eyelet 280 having a funnel shaped slot 282 entry therein for loading the tissue suture 254a into the eyelet and then inhibiting its passage back out of the slot 282. Anchor 252b (FIG. 16B) has an eyelet 284 formed of overlapping arms 286 creating a tortuous path 288 into the eyelet 284 for the tissue suture 254b. Anchor 252c (FIG. 16C) has a fork tip 290 formed of distally projecting tines 292 between which the tissue suture 254c can be captured.

FIGS. 17 and 18A to 18H illustrate a further embodiment of a suture anchor system 300 according to the present invention. It comprises a suture anchor 302 having an elongated cylindrical shape with an axial cannulation 304 and internal suture saddle 306. Annular barb-shaped flanges 308 encircle the anchor 302 to enhance its bone fixation. A suture 310 comprise a sliding knot 312 forming a collapsing loop 314 around the suture saddle 306 with a long fixed tail 316 and collapsing tail 318. A suture threader 320 comprises an elongated flexible threading wire 322 received through the cannulation 304 and terminating in a distal suture capture loop 324 distal of the anchor 302.

Figure 18A:
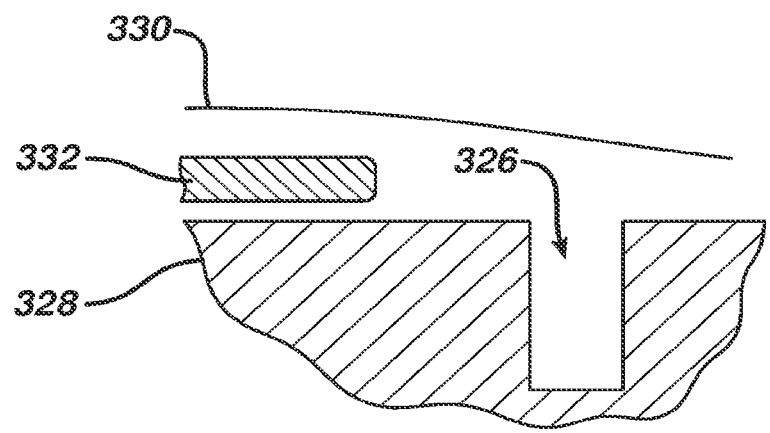
FIGS. 18A to 18H are front elevation views in cross-section of a method of using the suture anchor system of FIG. 17.
Figure 18B:
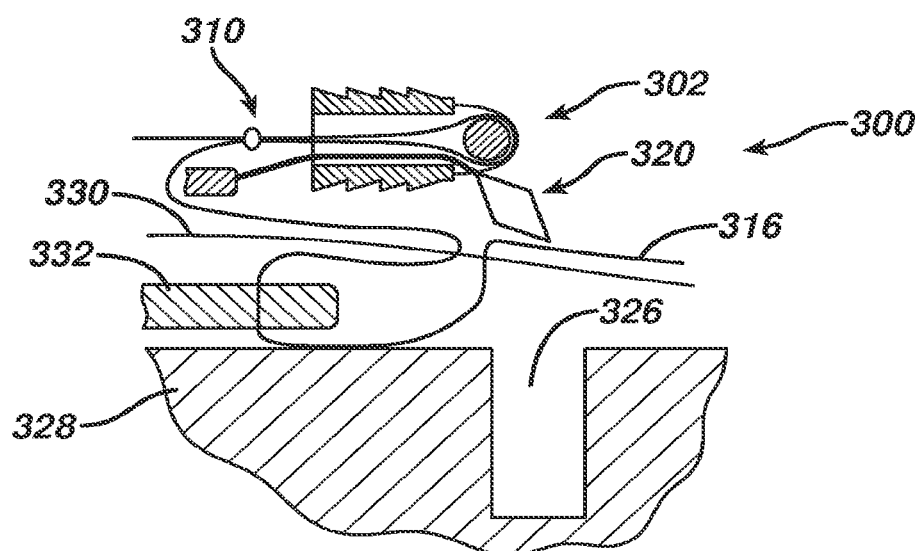
Figure 18C:
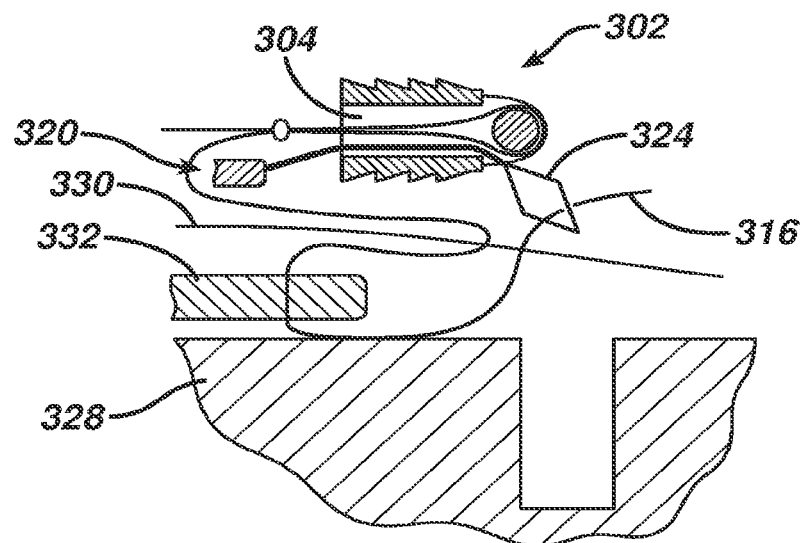
Figure 18D:
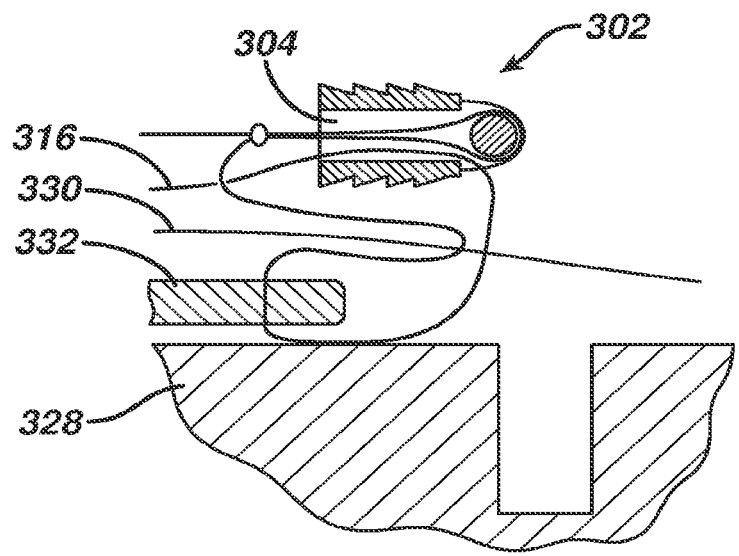
Figure 18E:
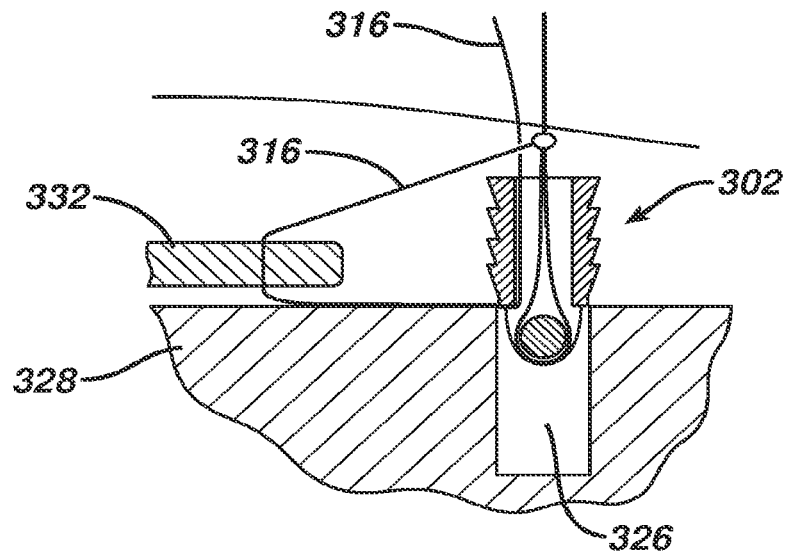
Figure 18F:
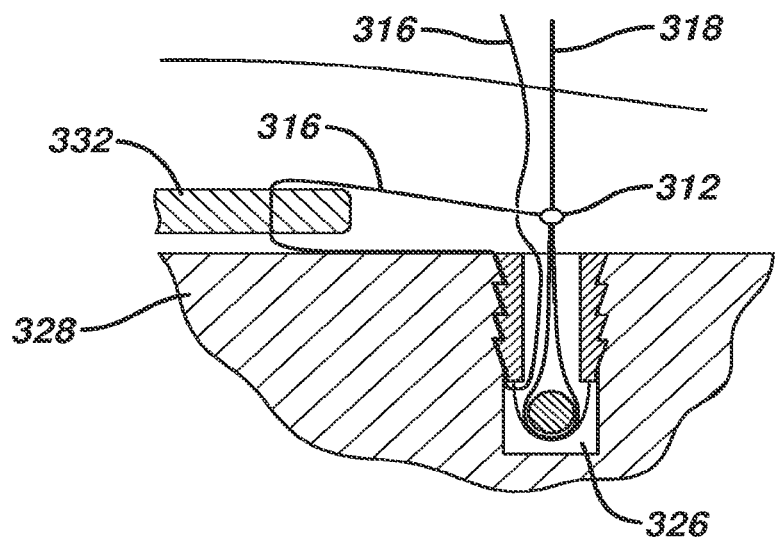
Figure 18G:
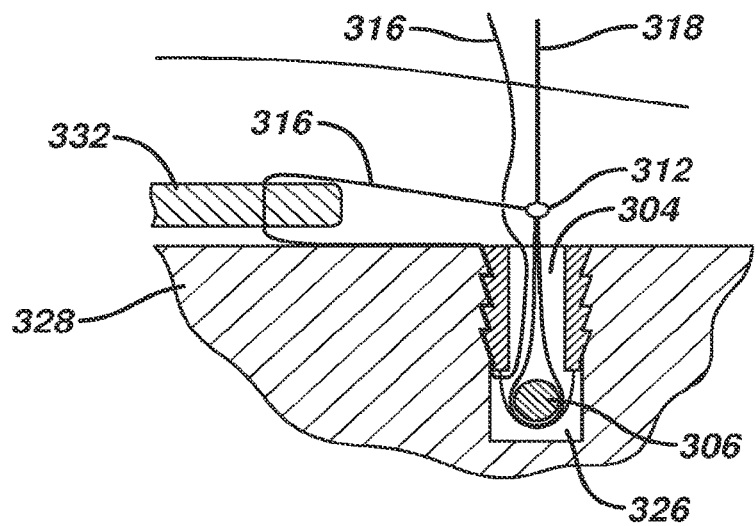
Figure 18H:
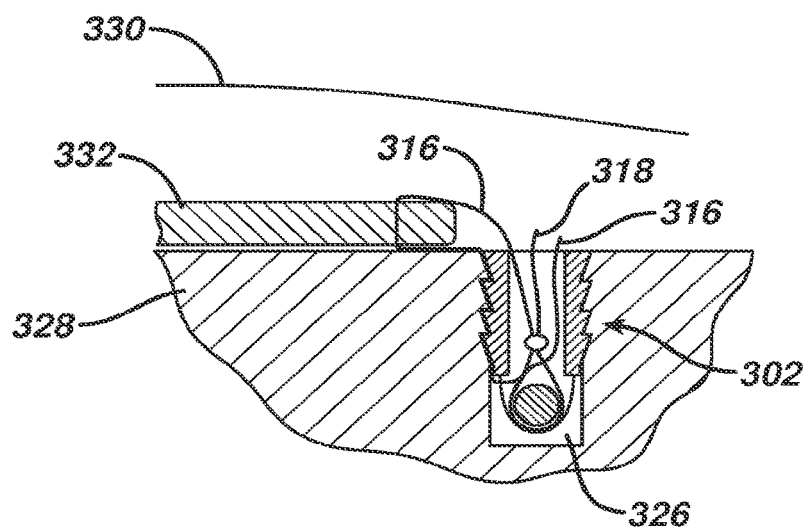

To employ the suture anchor system 300, a bone hole 326 is formed in a bone 328 beneath a patient's skin 330 and adjacent a soft tissue 332, such as for example a tendon, (FIG. 18A) which is to be attached to the bone 328 with the suture anchor system 300. The fixed tail 316 is passed through the soft tissue 332 and brought back outside of the skin 330 (FIG. 18B). As in the prior procedure descriptions the procedure is preferably performed arthroscopically and the associated arthroscopy equipment and the anchor driver are omitted from the FIGS. for clarity in illustrating the operation of the suture anchor system 300. The fixed tail 316 is loaded into the suture capture loop 324 (FIG. 18C) and the suture threader 320 is withdrawn proximally through the cannulation 304 to load the fixed tail 316 through the cannulation 304 (FIG. 18D). The suture anchor 302 is then placed into the opening of the bone hole 326 and the slack is taken out of the fixed tail 316 (FIG. 18E). When the suture anchor 302 is driven into the bone hole 326 it traps the fixed tail 316 between the anchor 302 and the bone 328 (FIG. 18F). By pulling on the collapsing tail 318 the collapsing knot 312 collapses the loop 304 and moves down toward the suture saddle 306 thereby drawing fixed tail 316 and thereby the soft tissue 332 toward the anchor 302 (FIG. 18G). The collapsing tail 318 and fixed tail 316 can then be trimmed completing the procedure (FIG. 18H). The resulting knot is very strong as tension between the fixed tail 316 where it leaves the knot 312 and the loop 314 cinches the knot and such tension is provided by the load between the soft tissue 332 and the suture saddle 306 thus providing a strong fixation.

The novel suture anchors of the present invention may be made from a number of suitable materials including a metallic material, a non-biodegradable polymer, a biodegradable polymer, or a composite of a biodegradable polymer or copolymer and a bioceramic. The term biodegradable as used herein is defined to mean materials that degrade in the body and then are either absorbed into or excreted from the body. The term bioceramic as defined herein is defined to mean ceramic and glass materials that are compatible with body tissue. The bioceramics are preferably biodegradable.

The metallic materials that can be used to manufacture the anchors of the present invention include stainless steel, titanium, alloys of nickel and titanium, or other biocompatible metallic materials.

The non-biodegradable materials that can be used to manufacture the anchors of the present invention include polyethylene, polypropylene, PEEK (polyetheretherketone), or other biocompatible non-absorbable polymers.

The biodegradable polymers that can be used to manufacture the anchors used in the present invention include biodegradable polymers selected from the group consisting of aliphatic polyesters, polyorthoesters, polyanhydrides, polycarbonates, polyurethanes, polyamides and polyalkylene oxides. Preferably, the biodegradable polymers are aliphatic polyester polymers and copolymers, and blends thereof. The aliphatic polyesters are typically synthesized in a ring opening polymerization. Suitable monomers include but are not limited to lactic acid, lactide (including L-, D-, meso and D,L mixtures), glycolic acid, glycolide, .epsilon.-caprolactone, p-dioxanone (1,4-dioxan-2-one), trimethylene carbonate (1,3-dioxan-2-one), .delta.-valerolactone, and combinations thereof.

The bioceramics that can be used in the composite anchors of the present invention include ceramics comprising mono-, di-, tri-, .alpha.-tri-, .beta.-tri-, and tetra-calcium phosphate, hydroxyapatite, calcium sulfates, calcium oxides, calcium carbonates, magnesium calcium phosphates. It is particularly preferred to use a .beta.-tritricalcium phosphate. In addition to bioceramics, bioglasses may also be used in the composite screws. The bioglasses may include phosphate glasses and bioglasses.

Suitable biocompatible synthetic polymers can include polymers selected from the group consisting of aliphatic polyesters, poly(amino acids), copoly(ether-esters), polyalkylene oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, polyurethanes, poly(ether urethanes), poly(ester urethanes), poly(propylene fumarate), poly(hydroxyalkanoate) and blends thereof.

For the purpose of this invention aliphatic polyesters include, but are not limited to, homopolymers and copolymers of lactide (which includes lactic acid, D-,L- and meso lactide); glycolide (including glycolic acid); .epsilon.-caprolactone; p-dioxanone (1,4-dioxan-2-one); trimethylene carbonate (1,3-dioxan-2-one); alkyl derivatives of trimethylene carbonate; .delta.-valerolactone; .beta.-butyrolactone; .gamma.-butyrolactone; .epsilon.-decalactone; hydroxybutyrate; hydroxyvalerate; 1,4-dioxepan-2-one (including its dimer 1,5,8,12-tetraoxacyclotetradecane-7,14-dione); 1,5-dioxepan-2-one; 6,6-dimethyl-1,4-dioxan-2-one; 2,5-diketomorpholine; pivalolactone; .alpha.,.alpha. diethylpropiolactone; ethylene carbonate; ethylene oxalate; 3-methyl-1,4-dioxane-2,5-dione; 3,3-diethyl-1,4-dioxan-2,5-dione-; 6,6-dimethyl-dioxepan-2-one; 6,8-dioxabicycloctane-7-one and polymer blends thereof. Additional exemplary polymer or polymer blends include, by non-limiting example, a polydioxanone, a polyhydroxybutyrate-co-hydroxyvalerate, polyorthocarbonate, a polyaminocarbonate, and a polytrimethylene carbonate. Aliphatic polyesters used in the present invention can be homopolymers or copolymers (random, block, segmented, tapered blocks, graft, triblock, etc.) having a linear, branched or star structure. Poly(iminocarbonates), for the purpose of this invention, are understood to include those polymers as described by Kemnitzer and Kohn, in the Handbook of Biodegradable Polymers, edited by Domb, et. al., Hardwood Academic Press, pp. 251-272 (1997). Copoly(ether-esters), for the purpose of this invention, are understood to include those copolyester-ethers as described in the Journal of Biomaterials Research, Vol. 22, pages 993-1009, 1988 by Cohn and Younes, and in Polymer Preprints (ACS Division of Polymer Chemistry), Vol. 30(1), page 498, 1989 by Cohn (e.g., PEO/PLA). Polyalkylene oxalates, for the purpose of this invention, include those described in U.S. Pat. Nos. 4,208,511; 4,141,087; 4,130,639; 4,140,678; 4,105,034; and 4,205,399. Polyphosphazenes, co-, ter- and higher order mixed monomer based polymers made from L-lactide, D,L-lactide, lactic acid, glycolide, glycolic acid, para-dioxanone, trimethylene carbonate and E-caprolactone such as are described by Allcock in The Encyclopedia of Polymer Science, Vol. 13, pages 31-41, Wiley Intersciences, John Wiley & Sons, 1988 and by Vandorpe, et al in the Handbook of Biodegradable Polymers, edited by Domb, et al., Hardwood Academic Press, pp. 161-182 (1997). Polyanhydrides include those derived from diacids of the form HOOC—C.sub.6H.sub.4-O—(—CH.sub.2).sub.m-O—C.sub.6H.sub.4-COOH, where "m" is an integer in the range of from 2 to 8, and copolymers thereof with aliphatic alpha-omega diacids of up to 12 carbons. Polyoxaesters, polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150. Polyorthoesters such as those described by Heller in Handbook of Biodegradable Polymers, edited by Domb, et al., Hardwood Academic Press, pp. 99-118 (1997).

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A method of attaching a soft tissue to a bone, the method comprising the steps of:
   passing a tissue suture through a piece of soft tissue;
   implanting a suture anchor into the bone; and
   collapsing a collapsible suture loop that is affixed to the anchor and connected to the tissue suture and thereby tensioning the tissue suture,
   wherein the collapsible suture loop is defined by a sliding knot, and a fixed tail and a collapsing tail extend from the sliding knot from a side of the sliding knot that is opposite of a side of the sliding knot from which the collapsible suture loop extends, the fixed tail being stationary with respect to the sliding knot such that a length of the fixed tail is fixed with respect to the sliding knot, and
   wherein the collapsing step further includes tensioning the collapsing tail.

2. The method of claim 1 and further comprising the step of trapping a first portion of the tissue suture between the suture anchor and the bone.

3. The method of claim 2 and further comprising the steps of passing a second portion of the tissue suture, adjacent the first portion of the tissue suture, through an axial cannulation through the suture anchor prior to implanting the anchor into the bone.

4. The method of claim 3 and further comprising the step of threading the second portion through the cannulation via a suture grasper passed through the cannulation by loading the second portion into a suture capture mechanism of the suture grasper located distal of the anchor and then pulling the suture grasper, including the suture capture mechanism, proximally through the cannulation.

5. The method of claim 2 wherein when the tissue suture is trapped between the suture anchor and the bone, the soft tissue is disposed on the tissue suture between the first portion and where the tissue suture connects to the collapsible loop.

6. The method of claim 2 and further comprising the step of engaging the tissue suture at a distal end of the suture anchor prior to implanting the anchor into the bone.

7. The method of claim 6 wherein the step of engaging the tissue suture at the distal end of the anchor comprises loading the tissue suture into an eyelet located at the distal end of the anchor.

8. The method of claim 1 and further comprising restraining the collapsible loop via a post affixed to the suture anchor and passing through the collapsible loop.

9. The method of claim 1 wherein the collapsible suture loop further comprises a noose having a loop portion, and the sliding knot closing the loop portion.

10. The method of claim 9 wherein the anchor comprises a central axial cannulation with the loop portion and the collapsing tail extending proximally thereout and wherein the step of collapsing the loop portion draws the loop portion distally into the cannulation.

11. The method of claim 10 wherein the tissue suture extends from the soft tissue as a loop which interconnects with the collapsible loop and wherein the step of collapsing the collapsible loop tensions the loop of tissue suture.

12. The method of claim 9 wherein the anchor comprises a central axial cannulation with the fixed tail of the sliding knot and the collapsing tail extending proximally thereout and wherein the fixed tail is passed through the soft tissue to become the tissue suture.

13. The method of claim 1 and further comprising removing slack from the tissue suture prior to the step of implanting the suture anchor into the bone.

14. The method of claim 1, further comprising threading the tissue suture from a distal end of the suture anchor to a proximal end of the suture anchor.

15. A surgical method comprising:
    passing a tissue suture through a piece of soft tissue;
    threading a terminal end of the tissue suture through a suture anchor having an axial cannulation extending from a proximal end opening and through to a distal end opening of the suture anchor, the terminal end of the tissue suture being passed through the axial cannulation of the suture anchor from the distal end opening of the suture anchor to the proximal end opening of the suture anchor;
    implanting the suture anchor into a bone and causing a portion of the tissue suture to be locked between the suture anchor and the bone; and
    collapsing a collapsible suture loop that is affixed to the suture anchor and extends through the axial cannulation out of the proximal end opening of the suture anchor, the collapsible suture loop being connected to the tissue suture and thereby tensioning the tissue suture.

16. The method of claim 15, wherein a suture grasper is used to perform the threading step.

17. The method of claim 15, wherein the collapsible suture loop is further defined by a sliding knot, and a fixed tail and a collapsing tail extend from the sliding knot, through the axial cannulation, and out of the proximal end of the suture anchor.

18. The method of claim 17, wherein the fixed tail is passed through the soft tissue to become the tissue suture.

19. A method of securing tissue, the method comprising:
    passing a first portion of suture through a piece of tissue;
    implanting a suture anchor into a bone, the suture anchor having an axial cannulation extending between a proximal end and a distal end of the suture anchor and having a collapsible suture loop secured thereto, the collapsible suture loop being coupled to the piece of tissue through which the first portion of suture is passed, the collapsible loop being defined by a sliding knot, and a fixed tail and a collapsing tail extending from a side of the sliding knot that is opposite of a side of the sliding knot from which the collapsible suture loop extends;
    attaching the suture to a suture grasper;
    passing the suture grasper from a location that is distal of the distal end of the suture anchor, through the axial cannulation to a location that is proximal of the proximal end of the suture anchor; and
    collapsing the collapsible suture loop that is secured to the suture anchor and to the tissue by tensioning the collapsing tail.

20. The method of claim 19, wherein the first portion of suture extends from the piece of the tissue as a loop which interconnects with the collapsible loop and wherein the step of collapsing the collapsible loop tensions the loop of the first portion of suture.

21. The method of claim 19, wherein the fixed tail is passed through the soft tissue to become the first portion of suture.

22. The method of claim 19 further comprising the step of trapping at least a part of the first portion of suture between the suture anchor and the bone.

* * * * *